(12) United States Patent
Kerns et al.

(10) Patent No.: US 7,928,178 B2
(45) Date of Patent: Apr. 19, 2011

(54) RUBBER FOR BABY BOTTLE NIPPLES, PACIFIERS, AND SYRINGE PLUNGERS

(75) Inventors: Michael Lester Kerns, Medina, OH (US); Michael Joseph Rachita, North Canton, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 285 days.

(21) Appl. No.: 10/868,160

(22) Filed: Jun. 15, 2004

(65) Prior Publication Data

US 2004/0230017 A1 Nov. 18, 2004

Related U.S. Application Data

(60) Division of application No. 10/808,856, filed on Mar. 25, 2004, which is a division of application No. 10/273,918, filed on Oct. 18, 2002, now Pat. No. 6,871,751, and a continuation-in-part of application No. 10/273,918, filed on Oct. 18, 2002, now Pat. No. 6,871,751.

(60) Provisional application No. 60/359,695, filed on Oct. 19, 2001, provisional application No. 60/412,833, filed on Sep. 23, 2002.

(51) Int. Cl.
| C08F 36/00 | (2006.01) |
| C08F 10/00 | (2006.01) |
| A61J 9/00 | (2006.01) |
| A61J 9/04 | (2006.01) |
| A61J 7/00 | (2006.01) |
| A61M 5/315 | (2006.01) |

(52) U.S. Cl. ............ 526/335; 526/348.7; 215/11.1; 215/11.5; 604/78; 604/236

(58) Field of Classification Search ............ 215/11.1, 215/11.5; 604/78, 236; 526/335, 348.7
See application file for complete search history.

(56) References Cited

U.S. PATENT DOCUMENTS

| 3,297,667 | A | 1/1967 | Von Dohlen et al. | 260/82.1 |
|---|---|---|---|---|
| 3,676,411 | A | 7/1972 | Throckmorton et al. | 260/82.1 |
| 3,794,604 | A | 2/1974 | Throckmorton et al. | 252/431 C |
| 4,030,498 | A | 6/1977 | Tompkins | 128/218 P |
| 4,180,069 | A | 12/1979 | Walters | 128/218 P |
| 4,242,232 | A | 12/1980 | Sylvester et al. | 252/429 C |
| 4,258,714 | A | 3/1981 | Leopoldi et al. | 128/232 |
| 4,260,707 | A | 4/1981 | Sylvester et al. | 526/114 |
| 4,405,317 | A | 9/1983 | Case | 604/90 |
| 4,412,836 | A | 11/1983 | Brignola | 604/87 |
| 4,429,089 | A | 1/1984 | Pedretti et al. | 526/153 |
| 4,444,903 | A | 4/1984 | Carbonaro et al. | 502/102 |
| 4,461,883 | A | 7/1984 | Takeuchi et al. | 526/139 |
| 4,533,711 | A | 8/1985 | Takeuchi et al. | 526/340.4 |
| 4,663,405 | A | 5/1987 | Throckmorton | 526/144 |
| 4,676,386 | A | 6/1987 | Phlaphongpanich | 215/11 R |
| 4,696,475 | A | 9/1987 | Tomita et al. | 472/365 |
| 4,699,960 | A | 10/1987 | Gordini et al. | 526/81 |
| 4,701,165 | A | 10/1987 | DeHaitre | 604/228 |
| 5,114,415 | A | 5/1992 | Shedlock | 604/319 |
| 5,653,732 | A | 8/1997 | Sheehy | 606/236 |

(Continued)

*Primary Examiner* — William K Cheung
(74) *Attorney, Agent, or Firm* — Alvin T. Rockhill

(57) ABSTRACT

The production of a protein free synthetic polyisoprene which has both low levels of chemical impurities and good physical properties has yet to be realized. It has now been envisioned that the use of neodymium catalyzed polyisoprene will offer the combined advantages of both a clean, as well as, high cis-1,4 polymer. Synthesis of polyisoprene rubber using a neodymium based catalyst system is described.

20 Claims, 17 Drawing Sheets

U.S. PATENT DOCUMENTS

| | | | |
|---|---|---|---|
| 5,659,101 A | 8/1997 | Biagini et al. | 585/601 |
| 5,686,371 A | 11/1997 | Ansell et al. | 502/102 |
| 5,699,921 A | 12/1997 | Rodriguez | 215/11.5 |
| 5,779,668 A | 7/1998 | Grabenkort | 604/89 |
| 5,785,682 A | 7/1998 | Grabenkort | 604/82 |
| 5,823,998 A | 10/1998 | Yamagata | 604/131 |
| 5,876,372 A | 3/1999 | Grabenkort et al. | 604/89 |
| 6,001,478 A * | 12/1999 | Apecetche et al. | 428/407 |
| 6,136,937 A | 10/2000 | Lai et al. | 526/133 |
| 6,194,505 B1 | 2/2001 | Sone et al. | 524/432 |
| 6,196,998 B1 | 3/2001 | Jansen et al. | 604/111 |
| 6,217,550 B1 | 4/2001 | Capes | 604/110 |
| 6,221,447 B1 * | 4/2001 | Munn et al. | 428/34.9 |
| 6,241,112 B1 | 6/2001 | Claessens et al. | 215/247 |
| 6,253,935 B1 | 7/2001 | Fletcher | 215/11.1 |
| 6,255,416 B1 | 7/2001 | Sone et al. | 526/153 |

* cited by examiner

Linear Correlation between Mooney Viscosity and Molecular Weight

Conversion vs Time at Various Nd Levels and TIBA Ratios

Dependence of Activity on Aging Time in Preformed Catalyst

First Order Rate Plots

Isoprene Homopolymerization Activation Energy

Comparison of Mooney vs Molecular Weight between
In-Situ and Preformed Catalysts Light scattering response versus Time between Nd-PI and Ti-PI Cumulative weight fraction versus molar mass between Nd-PI and Ti-PI

RUBBER FOR BABY BOTTLE NIPPLES, PACIFIERS, AND SYRINGE PLUNGERS

This application is a divisional and continuation-in-part of U.S. patent application Ser. No. 10/808,856 filed on Mar. 25, 2004 (now pending), which is a divisional and continuation-in-part application of U.S. patent application Ser. No. 10/273,918 filed on Oct. 18, 2002 (now issued as U.S. Pat. No. 6,871,751), which claims the benefit of U.S. Provisional Patent Application Ser. No. 60/359,695, filed on Oct. 19, 2001, and U.S. Provisional Patent Application Ser. No. 60/412,833, filed on Sep. 23, 2002.

BACKGROUND OF THE INVENTION

The use of natural rubber in the medical and health care industries can expose atopic individuals to latex allergens. It is believed that as much as 6% of the general population, and as high as 12% of those working in the medical profession, are latex sensitive and display allergic reactions when exposed to proteins found in natural rubber (see M. McNulty, *Rubber & Plastics News* Jun. 25, 2001, page. 5). The symptoms of latex allergy range from mild contact dermatitis to life-threatening anaphylaxis, which includes a rapid drop in blood pressure and difficulty breathing. Even though a heightened awareness of latex allergy now exists, the number of people becoming sensitized to natural rubber is increasing as more professions require the use of latex gloves to avoid exposure to infectious agents. It is therefore not surprising, that with over 40,000 consumer products containing natural rubber (see Information from Allergy Advisor-Zing Solutions, http://allergyadvisor.com) an alternative protein free material is desired in many applications.

Although techniques exist for enzymatic deproteinization of natural rubber (see S. Kawahara, T. Kakubo, N. Nishiyama, Y. Tanaka, Y. Isono, J. T. Sakdapipanich, *J. Appl. Polym. Sci.* 78, 1510 (2000) and A. H. Eng, S. Kawahara, Y. J. Tanaka, *Nat. Rubb. Res.* 8, 109 (1993), as well as manufacturing practices that lower the total allergens present in latex goods, currently, the most effective way to provide protein free products is to use petrochemical derived synthetic rubbers. In fact, a report from the Johns Hopkins University School of Medicine recommended that the Food and Drug Administration mandate a switch from using stoppers made with natural rubber to using all synthetic rubber medicine stoppers (again see M. McNulty, *Rubber & Plastics News* Jun. 25, 2001). The synthetic rubber most closely related to natural rubber (NR), is high cis-polyisoprene. Typically, this material is prepared through the use of either stereospecific titanium catalysts or with alkyl-lithium initiators. Both of these systems are effective at providing protein free synthetic polyisoprene, however, the two polymers differ greatly with respect to their micro- and macrostructure. Polymerization of isoprene with titanium tetrachloride activated with a trialkylaluminum co-catalyst results in a material with upwards of 98% 1,4-cis content (see W. Cooper, in W. M. Saltman, ed., *The Stereo Rubbers*, John Wiley & Sons, New York, 1977, page 48). Polyisoprene produced commercially with alkyl lithium initiators generally does not have a cis content higher than 92%. Differences in microstructure, as well as macrostructure, allows the titanium polyisoprene (Ti-PI), but not the lithium polyisoprene (Li-PI), to display the unique advantage of strain-induced crystallization. It is the property of rapid crystallization that allows NR and Ti-PI to have high tensile strength and modulus even without the use of reinforcing fillers, a condition often found in gum stocks commonly used in the production of medical goods (see A. R. Bean, Jr., et. al., in H. F. Mark, N. G. Gaylord, N. M. Bikales, ed., *Encyclopedia of Polymer Science and Technology*, John Wiley & Sons, New York, Vol. 7, 1967, page. 823). Although Li-PI lacks the microstructural regularity of Ti-PI, it does have the advantage of being gel free with a narrow molecular weight distribution and linear macrostructure. These attributes allow Li-PI to display lower hysteretic properties at a lower cross-link density than NR or Ti-PI.

The use of Ti-PI and Li-PI in the medical and health care industries has gained acceptance, yet there is still need for a number of improvements. For example, the consistency of Ti-PI is very dependent on the aluminum to titanium ratio that is used during catalyst preparation (see W. Cooper, in W. M. Saltman, ed., *The Stereo Rubbers*, John Wiley & Sons, New York, 1977, page 48). If the ratio drops below unity the titanium is not sufficiently reduced, causing the formation of gel in the polymer. On the other hand, if the catalyst is over-reduced, oligomers will be produced giving the material a strong odor. Both of these unwanted side reactions must be carefully controlled. Current titanium systems also suffer from inferior activity and high levels of titanium must be used resulting in elevated levels of catalyst residues and terminating agents in the finished polymer. An overall reduction in foreign substances remaining in synthetic polyisoprene is of paramount importance when the production of a clean high performance material is desired.

Li-PI is considered a clean polymer due to the use of low levels of initiator during production and lack of extractables. However, the dependence of cis content on lithium concentration leads to a polymer with very high molecular weight (see H. L. Hsieh, R. P. Quirk, *Anionic Polymerization Principles and Practical Applications*, Marcel Dekker, Inc., New York, 1996, p. 201). The high molecular weight, coupled with a narrow molecular weight distribution, makes processing this material difficult. Commonly a low molecular weight fraction is added to commercial material to act as a processing aid.

It has now been envisioned that the use of neodymium catalyzed polyisoprene (Nd-PI), as a source of protein free synthetic natural rubber, may offer the combined advantages of both Ti-PI and Li-PI without their respective disadvantages. It is expected that Nd-PI with a cis 1,4-content as high as 98%, gel and oligomer free, linear with a moderate molecular weight distribution, easy to process, and low in volatile and extractable residues will be ideally suited for many clean high performance applications. A discussion of the synthesis, characterization, and compounded properties of this material is presented.

SUMMARY OF THE INVENTION

The production of a protein free synthetic polyisoprene, which has both low levels of chemical impurities and good physical properties, has yet to be realized. It has now been envisioned that the use of neodymium catalyzed polyisoprene will offer the combined advantages of both a clean, as well as, high cis-1,4 polymer. Synthesis of polyisoprene rubber using a neodymium based catalyst system is described. Characterization of the material shows the absence of an ultra high molecular weight fraction and the presence of very high cis-1,4-microstructure. Gum stock and black filled compound studies comparing neodymium polyisoprene with natural rubber, titanium polyisoprene, and lithium polyisoprene have been performed. Results indicate that Nd-PI has similar stress-strain and tear properties as synthetic titanium polyisoprene. Analysis of residual volatile, extractable, and oligomer levels indicates Nd-PI is indeed a clean source of high cis synthetic polyisoprene. In the practice of this invention such Nd-PI is used in manufacturing articles used in manufacturing health care products, garments, clothing, and food and beverage packaging. Some specific applications include: bandages, drug delivery patches, suture tape, pharmaceutical closures, including syringe plungers and sleeves, vial closures and stoppers, tourniquets, exercise bands, condoms and prophylactic devices, gloves and glove dip, intervenous bags and tubing, baby bottle nipples, pacifiers, and teething devices, breast hoods, and dental and orthodontic devices.

The present invention more specifically discloses a nipple, comprising: a fastening means including a sealing surface adapted to be fastened on a baby bottle, and a means forming a wall adapted to be contacted with a baby's mouth, said wall having at least one opening to allow milk to pass through, said wall means including a nipple portion with said opening being provided in said nipple portion, wherein said means forming said wall is comprised of polyisoprene rubber made with a neodymium catalyst.

The subject invention further discloses a nipple, comprising: (a) a mouth portion of orthodontic shape and having a skirt with an annular appendage of U-shaped cross-section, wherein said mouth portion is comprised of polyisoprene rubber made with a neodymium catalyst, and (b) a base portion made of a semi-rigid polymer and formed around the skirt of the mouth portion to interlock with the appendage, the base portion having a tubular portion that lies inside the skirt and presses outwardly against the appendage.

The subject invention also discloses a nipple, comprising: (a) a mouth portion of orthodontic form and having a generally tubular skirt, wherein said mouth portion is comprised of polyisoprene rubber made with a neodymium catalyst, and (b) a base portion made of semi-rigid polymer, the base portion having a cavity of annular form, which cavity is concentric with the skirt of the mouth portion, wherein the cavity, has a U-shaped cross-section defined by a first tubular leg having an opening onto an outer surface of the base portion and a second tubular leg concentric with the first leg and joined to it by a radial passage, the skirt of the mouth portion entering the cavity through the opening into the first leg, filling the first leg, the radial passage, and the second leg to lock the mouth portion securely to the base portion.

The present invention further reveals a breast hood adapted to be connected to a milk pump, said breast hood comprising a wall means forming an outer surface and an inner surface, said inner surface being substantially conical so as to have a wide opening end for engaging a female breast, and a small opening end, said outer surface being of a first, relative rigid material, while said inner surface is of polyisoprene rubber made with a neodymium catalyst.

The subject invention also discloses a pacifier comprised of a mouth portion and a base portion, wherein said mouth portion is comprised of polyisoprene rubber made with a neodymium catalyst.

The present invention further discloses a syringe which is comprised of a barrel having a fluid chamber, a proximal end, a distal end and an elongated tip extending from said distal end having a passageway therethrough in fluid communication with said chamber, and an elongated plunger rod including a stopper slidably positioned in fluid-tight engagement with an inside surface of said chamber for drawing fluid into and out of said chamber by movement of said plunger relative to said barrel, wherein the stopper is comprised of neodymium polyisoprene rubber.

The subject invention further reveals a syringe comprising: a barrel having a fluid chamber, a proximal end, a distal end and an elongated tip extending from said distal end having a passageway therethrough in fluid communication with said chamber; and a plunger including an elongated plunger rod having a longitudinal axis, a proximal portion and a distal portion connected by a breakable connection, one of said proximal portion and said distal portion including an axial projection having a plurality of transverse protuberances projecting therefrom, said protuberances being connected to the other of said proximal portion and said distal portion, said breakable connection being on said protuberances, said distal portion including a stopper slidably positioned in fluid-tight engagement with an inside surface of said chamber for drawing fluid into and out of said chamber by movement of said plunger relative to said barrel, wherein the stopper is comprised of neodymium polyisoprene rubber, said breakable connection being strong enough to hold said proximal portion and said distal portion together during normal use of said syringe and breakable upon application of an additional force applied to said proximal portion along said longitudinal axis.

The subject invention also reveals a syringe that is comprised of a barrel defining a bore and having a discharge portion, and a plunger extending into said bore and movable therewithin, in combination with an inner sealing means carried by said plunger and movable axially within said bore in an area proximate to said discharge portion for substantially preventing leakage of medicament or other biologic fluid contained in the space forward of said inner sealing means adjacent said discharge portion; outer sealing means carried by said plunger, said outer sealing means being spaced axially from said inner sealing means and movable axially within said bore in an area behind the travel area of said inner sealing means; said plunger having an axial length within the bore of more than one-half of the functional length of the bore void of sealing rings; and means for preventing said outer sealing means from moving in the area in which said inner sealing means travels, wherein said sealing means is comprised of neodymium polyisoprene rubber.

The present invention further discloses an injection apparatus, comprising an ampule having a piston for sealing an agent in a syringe, comprising: piston rod means for pressing the piston of the ampule in an axial direction; an ampule holding part having an ampule insertion outer opening, having an original circumference, which opening is expanded circumferentially when the ampule is inserted into the opening and having an ampule insertion space for inserting the ampule thereinto, wherein the outer opening is restored to its original circumference after the ampule is inserted into the ampule insertion space, so that the ampule is held by the ampule holding part temporarily; and ampule gripping means for gripping the ampule and preventing axial movement thereof wherein a concave part is formed on a peripheral surface of the piston rod, wherein the concave part comprises a bottom surface generally parallel with an inner peripheral surface of the guide sleeve, a front step surface being provided on a front side of the bottom surface and extending from the bottom surface outwardly in a radial direction of the piston rod, and a rear step surface being provided on a rear side of the bottom surface and extending from the bottom surface outwardly in the radial direction of the piston rod, and wherein the piston rod means further comprises spring means for automatically returning the screw rod and the piston rod to the initial position when a force for pushing in the screw rod and the piston rod is released, and a stopper member which is positioned in the concave of the piston rod, slides in contact with the bottom surface of the piston rod and the inner peripheral surface of the guide sleeve with a predetermined frictional force, moves together with the piston rod with the stopper member in contact with the rear step surface of the piston rod when the piston rod is pushed in, and stops the movement of the piston rod with the stopper member in contact with the front step surface of the piston rod when the piston rod is returned by the spring means, wherein a frictional force between the stopper member and the bottom surface of the piston rod is smaller than an automatic return force of the spring means; and a frictional force between the stopper member and the inner peripheral surface of the guide sleeve is greater than the automatic return force of the spring means, wherein the stopper member is comprised of neodymium polyisoprene rubber.

The subject invention also discloses a syringe assembly comprising an outer barrel for a powder medicament, an inner barrel telescopically mounted in the outer barrel for diluent, seal means isolating the powder and diluent compartments comprising a plug member made of a resilient material sealingly engaging in the discharge opening of the inner barrel, plunger means mounted on the discharge end of the inner barrel including a hollow plug chamber closed at one end remote from the discharge end of the inner barrel by a wall having a plurality of discharge openings therein, said plug member including a pintle projecting from one axial end face thereof of said plug member of a diameter less than the body portion of said plug member and greater than the discharge openings in said plunger end wall, said plug member adapted upon pressure buildup in the inner barrel to be displaced axially outwardly into said plug chamber to permit flow of diluent from the inner barrel to the powder compartment, wherein the plug member and/or plunger are comprised of neodymium polyisoprene rubber.

The present invention further reveals a syringe mixing and delivery system comprising a first barrel having an open end and an opposite delivery end defining a delivery passage; a reciprocable stopper sealingly disposed in said first barrel to define a first chamber between said delivery passage and said reciprocable stopper for containing a first constituent in said first chamber; a second barrel that is sized to be disposed in said first barrel and that has an open end and an opposite discharge end defining a discharge passage; a slidable plunger sealingly disposed within said second barrel to define a second chamber between said discharge passage and said slidable plunger for containing a liquid second constituent in said second chamber; and fluid transfer connector means for operatively connecting said second barrel with said reciprocable stopper to permit flow of said liquid second constituent through said stopper from said second chamber to said first chamber to mix with said first constituent when said second barrel discharge end and plunger are moved closer together whereby subsequent movement of said second barrel and reciprocable stopper together toward said delivery passage of said first barrel expresses the mixed constituents out of said first chamber through said delivery passage, wherein said reciprocable stopper and plunger are comprised of neodymium polyisoprene rubber.

The present invention also discloses a drug delivery system, comprising a first pre-filled syringe assembly comprising a first syringe barrel having an interior surface, an open end, and an opposite delivery end which defines a drug delivery passage; a reciprocable stopper slidably disposed within said first syringe barrel in sealing engagement therewith for defining an internal mixing chamber within said first syringe barrel in communication with said delivery passage; and a sterility maintenance sleeve extending from said reciprocable stopper toward said open end of said first syringe barrel, said sterility maintenance sleeve maintaining the sterility of the interior surface of said first syringe barrel; a second pre-filled syringe assembly comprising a second syringe barrel having a fluid discharge passage at one end thereof, said second syringe barrel being sized to be disposed within the sterility maintenance sleeve of said first syringe assembly a movable piston plunger positionable within said second syringe barrel to define a fluid chamber therewith in communication with said fluid discharge passage; and a liquid in the fluid chamber of said second syringe barrel; and said system further including fluid transfer connector means for providing fluid communication from the fluid chamber of said second syringe assembly to said internal mixing chamber of said first syringe assembly when said second syringe assembly is disposed within said sterility maintenance sleeve so that the liquid within said fluid chamber can be caused to flow through said fluid transfer connector means into said internal mixing chamber of said first syringe assembly by movement of said piston plunger toward said fluid discharge passage of said second syringe assembly and thereafter caused to flow from said mixing chamber of said first syringe assembly through said drug delivery passage by movement of said second syringe assembly together with said reciprocable stopper and said sterility maintenance sleeve toward the drug delivery passage of said first syringe assembly, said fluid transfer connector means includes means for regulating the flow of fluid through said reciprocable stopper, said reciprocable stopper has an outer side facing toward said open end of said first syringe barrel and an inner side facing toward said drug delivery passage, said means for regulating the flow of fluid through said reciprocable stopper comprises said reciprocable stopper having a resilient body with a longitudinal slit through the resilient body defining two normally closed resilient lips, and the resilient body of said reciprocable stopper is substantially hollow and includes an enlarged cavity and a smaller entrance passage; and said sterility maintenance sleeve further includes: an enlarged head for being received in said enlarged cavity un said enlarged cavity of said resilient body, a smaller neck for being received in said smaller entrance passage of said resilient body, and a radially extending support flange adjacent said smaller neck for axially supporting said reciprocable stopper outer side, wherein said reciprocable stopper is comprised of neodymium polyisoprene rubber.

The present invention further discloses a stopper for sealing infusion bottles containing pharmaceutical liquids, which stopper has a collar, which projects into the opening in the neck of the container and has a diameter greater than the neck opening; an edge, which rests on the neck of the container; and a puncture area, enclosed by the edge and the collar, the stopper being held on the neck of the container by a protective cap of metal or plastic, characterized in that the top surface of the puncture area is lower than the top surface of the edge, and in that the bottom surface of the stopper inside the collar as well as the top surface of the puncture area are relatively flat, and in that a transverse plane formed by end surface of container neck passes through approximately the center of the vertical thickness of the puncture area, and wherein the length of said collar is generally the same as the cross sectional thickness of the puncture area, the puncture area having a predetermined elasticity and flexibility with respect to the edge and the collar whereby after the stopper has been inserted into the neck of container, the puncture area bulges slightly outward and remains in that position until the puncture needle of an infusion kit has been inserted into the stopper, and in that the puncture area bulges down into neck of the container when being pierced by the puncture needle and remains in this position as long as the puncture needle is inserted into the stopper, wherein the puncture area of the stopper is made of neodymium polyisoprene rubber.

BRIEF DESCRIPTION OF THE DRAWINGS

Various embodiments of the subject invention are illustrated in the accompanying drawings in which.

DETAILED DESCRIPTION OF THE INVENTION

Figure 2:
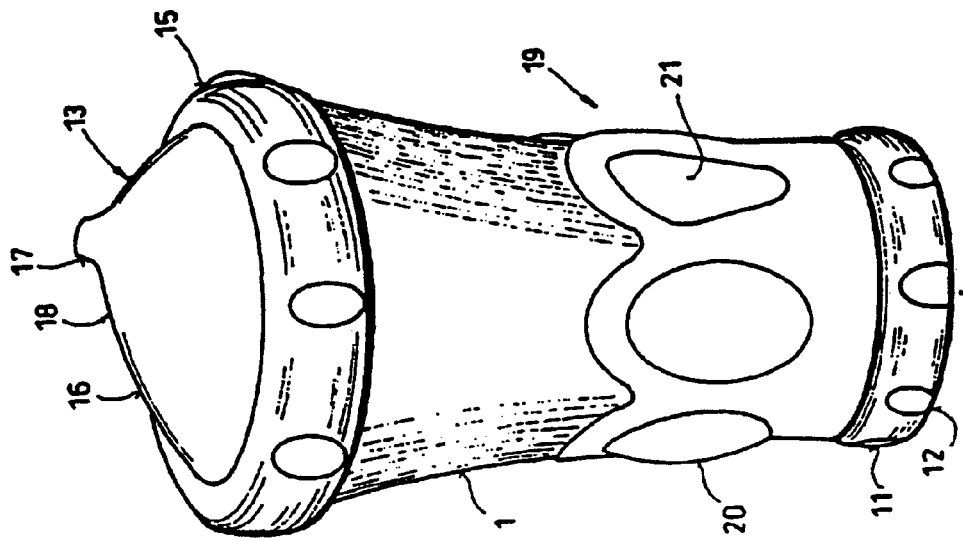
FIG. 2 is a somewhat enlarged perspective view of the baby's bottle and nipple combination when assembled.

In the practice of this invention polyisoprene rubber that is synthesized using a neodymium containing catalyst system is used in manufacturing health care products, garments, clothing, and food and beverage packaging. Some specific applications include: bandages, drug delivery patches, suture tape, medical devices, pharmaceutical closures, including syringe plungers and sleeves, needle shields, injection sites, vial closures and stoppers, tourniquets, exercise bands, cosmetics, condoms and prophylactic devices, gloves and glove dip, IV and other bags, tubing, clean room applications, baby bottle nipples and teething devices, dental and orthodontic applications, chewing gum and slow release delivery gums, food additives, packaging and delivery systems for food including beverage tubing, conveyor belting and rollers, seals and coatings, potable water systems, pet chew toys, adhesive tapes, duct tapes, labels, envelopes, sticky notes, coatings, sealants, including cold seal adhesives for candy wrappers, diaper tabs, elastic thread for garments and sporting goods, calendered stock for clothing, rubber bands, rubber grips for tools and appliances, liquid crystal encapsulation, wire, cable and component insulation, membranes, vacuum applications, computers and communication devices.

The catalyst systems to which this invention pertains are comprised of three components. These components are (1) an organoaluminum compound, (2) an organoneodymium compound, and (3) at least one compound that contains at least one labile halide ion. Such a neodymium catalyst system is described in U.S. patent application Ser. No. 10/368,660, filed on Feb. 18, 2003, the teachings of which are incorporated herein by reference.

The organoaluminum compound contains at least one carbon to aluminum bond and can be represented by the structural formula:

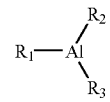

wherein $R_1$ is selected from the group consisting of alkyl (including cycloalkyl), alkoxy, aryl, alkaryl, arylalkyl radicals and hydrogen: $R_2$ is selected from the group consisting of alkyl (including cycloalkyl), aryl, alkaryl, arylalkyl radicals and hydrogen and $R_3$ is selected from a group consisting of alkyl (including cycloalkyl), aryl, alkaryl and arylalkyl radicals. Representative of the compounds corresponding to this definition are: diethylaluminum hydride, di-n-propylaluminum hydride, di-n-butylaluminum hydride, diisobutylaluminum hydride, diphenylaluminum hydride, di-p-tolylaluminum hydride, dibenzylaluminum hydride, phenylethylaluminum hydride, phenyl-n-propylaluminum hydride, p-tolylethylaluminum hydride, p-tolyl-n-propylaluminum hydride, p-tolylisopropylaluminum hydride, benzylethylaluminum hydride, benzyl-n-propylaluminum hydride, and benzylisopropylaluminum hydride and other organoaluminum hydrides. Also included are ethylaluminum dihydride, butylaluminum dihydride, isobutylaluminum dihydride, octylaluminum dihydride, amylaluminum dihydride and other organoaluminum dihydrides. Also included are diethylaluminum ethoxide and dipropylaluminum ethoxide. Also included are trimethylaluminum, triethylaluminum, tri-n-propylaluminum, triisopropylaluminum, tri-n-propylaluminum, triisopropylaluminim, tri-n-butylaluminum, triisobutylaluminum, tripentylaluminum, trihexylaluminum, tricyclohexylaluminum, trioctylaluminum, triphenylaluminum, tri-p-tolylaluminum, tribenzylaluminum, ethyldiphenylaluminum, ethyl-di-p-tolylaluminum, ethyldibenzylaluminum, diethylphenylaluminum, diethyl-p-tolylaluminum, diethylbenzylaluminum and other triorganoaluminum compounds.

In the organoneodymium compound a neodymium ion forms the central core of the compound to which ligand-type groups or atoms are joined. These compounds are sometimes known as coordination-type compounds. These compounds may be symbolically represented as $NdL_3$ wherein Nd represents neodymium and L is an organic ligand containing from 1 to 20 carbon atoms selected from a group consisting of (1) o-hydroxyaldehydes, (2) o-hydroxyphenones, (3) aminophenols, (4) hydroxy esters, (5) hydroxy quinolines, (6) beta-diketones, (7) monocarboxylic acids, (8) ortho dihydric phenols, (9) alkylene glycols, (10) dicarboxylic acids, (11) alkylated derivatives of dicarboxylic acids and (12) phenolic ethers.

In the organoneodymium compound utilized the organic portion includes organic type ligands or groups which contain from 1 to 20 carbon atoms. These ligands can be of the monovalent and bidentate or divalent and bidentate form. Representative of such organic ligands or groups are (1) o-hydroxyaldehydes such as salicylaldehyde, 2-hydroxyl-1-naphthaldehyde, 2-hydroxy-3-naphthaldehyde and the like; (2) o-hydroxyphenones such as 2'-hydroxyacetophenone, 2'-O-hydroxybutyrophenone, 2'-hydroxypropiophenone and the like: (3) aminophenols such as o-aminophenol, N-methyl o-aminophenol, N-ethyl o-aminophenol and the like: (4) hydroxy esters such as ethyl salicylate, propyl salicylate, butyl salicylate and the like: (5) phenolic compounds such as 2-hydroxyquinoline, 8-hydroxyquinoline and the like: (6) beta-diketones such as acetylacetone, benzoylacetone, propionylacetone, isobutyrylacetone, valerylacetone, ethylacetylacetone and the like; (7) monocarboxylic acids such as acetic acid, propionic acid, valeric acid, hexanoic acid, 2-ethylhexanoic acid, neodecanoic acid, lauric acid, stearic acid and the like: (8) ortho dihydric phenols such as pyrocatechol; (9) alkylene glycols such as ethylene glycol, propylene glycol, trimethylene glycol, tetramethylene glycol and the like: (10) dicarboxylic acids such as oxalic acid, malonic acid, maleic acid, succinic acid, o-phthalic acid and the like: (11) alkylated derivatives of the above-described dicarboxylic acids; (12) phenolic ethers such as o-hydroxyanisole, o-hydroxyethyl phenol ether and the like.

Representative organoneodymium corresponding to the formula $NdL_3$, which may be useful in the practice of this invention include neodymium naphthenate, neodymium neodecanoate, neodymium octanoate, and other neodymium metal complexes with ligands containing form 1 to 20 carbon atoms.

The third catalyst component utilized in the catalyst system is a compound that contains a halide ion. Some representative examples of halide ions that can be utilized include bromide ions, chloride ions, fluoride ions, and iodide ions. A combination of two or more of these ions can also be utilized. These halide ions can be introduced as (1) hydrogen halides: (2) alkyl, aryl, alkaryl, aralkyl and cycloalkyl metal halides wherein the metal is selected from the Groups II, III-A and IV-A of the Periodic Table; (3) halides of metals of Groups III, IV, V, VI-B and VIII of the Periodic Table and (4) organometallic halides corresponding to the general formula $ML_{(3-y)}X_y$, wherein M is a metal selected from the group consisting of metals of Group III-B of the Periodic Table having atomic numbers of 21, 39 and 57 through 71 inclusive: L is an organic ligand containing from 1 to 20 carbon atoms and selected from the group consisting of (a) o-hydroxyaldehydes, (b) o-hydroxyphenones, (c) hydroxyquinolines, (f) beta-diketones, (g) monocarboxylic acids, (h) ortho dihydric phenols, (i) alkylene glycols, (j) dicarboxylic acids, (k) alkylated derivatives of dicarboxylic acids and (1) phenolic ethers; X is a halide ion and y is an integer ranging from 1 to 2 and representing the number of halide ions attached to the metal M. The organic ligand L may be of the monovalent and bidentate or divalent and bidentate form.

Representative examples of such compounds containing a labile halide ion include (1) inorganic halide acids, such as hydrogen bromide, hydrogen chloride and hydrogen iodide: (2) organometallic halides, such as ethylmagnesium bromide, butylmagnesium bromide, phenylmagnesium bromide, methylmagnesium chloride, butylmagnesium chloride, ethylmagnesium iodide, phenylmagnesium iodide, diethylaluminum bromide, diisobutylaluminum bromide, methylaluminum sesquibromide, diethylaluminum chloride, ethylaluminum dichloride, ethylaluminum sesquichloride, diisobutylaluminum chloride, isobutylaluminum dichloride, dihexylaluminum chloride, cyclohexylaluminum dichloride, phenylaluminum dichloride, didodecylaluminum chloride, diethylaluminum fluoride, dibutylaluminum fluoride, diethylaluminum iodide, dibutylaluminum iodide, phenylaluminum diiodide, trimethyltin bromide, triethyltin chloride, dibutyltin dichloride, butyltin trichloride, diphenyltin dichloride, tributyltin iodide and the like; (3) inorganic halides, such as aluminum bromide, aluminum chloride, aluminum iodide, antimony pentachloride, antimony trichloride, boron tribromide, boron trichloride, ferric chloride, gallium trichloride, molybdenum pentachloride, phosphorus tribromide, phosphorus pentachloride, stannic chloride, titanium tetrachloride, titanium tetraiodide, tungsten hexachloride and the like: and (4) organometallic (Group III-B) halides, such as t-butylsalicylaldehydrocerium (III) chloride, salicylaldehydrocerium (III) chloride, 5-cyclohexylsalicylaldehydrocerium (III) chloride, 2-acetylphenolatocerium (III) chloride, oxalatocerium (III) chloride, oxalatocerium (III) bromide and the like. The preferred compounds that contain a labile halide ion are inorganic halide acids and organometallic halides.

The rare earth metal catalyst system can be prepared using an "in situ" technique or it can be "preformed." The term "in situ" means that the catalyst components are added separately from the isoprene monomer to be polymerized. The term "preformed" means that the catalyst components are mixed together prior to exposure of any of the components to the isoprene monomer to be polymerized. Freshly "preformed" catalysts that have been prepared in the absence of monomers are frequently more active than catalysts which have been allowed to age before use. Greatly improved "preformed" catalysts can be prepared by carrying out the "preforming" in the presence of small amounts of conjugated diolefins. Preforming in the presence of monomers results in homogeneous (soluble) catalyst systems, whereas those prepared by mixing in the absence of monomers are frequently heterogeneous (insoluble). Such a "preforming" technique is described in detail in U.S. Pat. No. 3,794,604 which is incorporated herein by reference.

The proportions of the components of the polymerization catalyst compositions of this invention can be varied widely. When the halide ion of the halogen containing compound is bromide, chloride or iodide ion, the atomic ratio of the halide ion to the neodymium metal can vary from about 0.1/1 to about 6/1. A more preferred ratio is from about 0.5/1 to about 3.5/1 and the most preferred ratio is about 2/1. However, when the halide ion of the halogen-containing compound is fluoride ion, the ratio of the fluoride ion to the neodymium metal ion ranges from about 20/1 to about 80/1 with the most preferred ratio being about 30/1 to about 60/1. The molar ratio of the trialkylaluminum or alkylaluminum hydride to neodymium metal can range from about 4/1 to about 200/1 with the most preferred range being from about 8/1 to about 100/1. The molar ratio of diolefin to neodymium metal can range from about 0.2/1 to 3000/1 with the most preferred range being from about 5/1 to about 500/1.

The amount of catalyst charged to the reduction system can be varied over a wide range: the sole requirement being that a catalytic amount of the catalyst composition, sufficient to cause polymerization of the isoprene monomer, be present in the reaction system. Low concentrations of catalyst are desirable in order to minimize ash problems. It has been found that polymerizations will occur when the catalyst level of the neodymium metal varies between 0.05 and 1.0 millimole of neodymium metal per 100 grams of monomer. A preferred ratio is between 0.1 and 0.3 millimole of neodymium per 100 grams of monomer.

The concentration of the total catalyst system employed of course, depends upon factors such as purity of the system, polymerization rate desired, temperature and other factors. Therefore, specific concentrations cannot be set forth except to say that catalytic amounts are used.

The polymerization of the isoprene monomer can be carried out by utilizing a bulk polymerization procedure, a vapor phase polymerization procedure, or a solution polymerization procedure employing suitable inert solvents. By the term "inert solvent" is meant that the solvent or diluent does not enter into the structure of, or affect adversely, the resulting polymer. Such solvents are usually aliphatic, aromatic and cycloaliphatic hydrocarbons, representative of which are pentane, hexane, heptane, benzene, toluene, cyclohexane and the like. The solvent/monomer volume ratio may be varied over a wide range. Up to 20 or more to 1 volume ratio of solvent to monomer can be employed. It is usually preferred, or more convenient, to use a solvent/monomer ratio of about 3/1 to about 6/1. In bulk polymerization procedures the reaction medium is substantially solvent-less and will contain no more than about 10% organic compounds that are solvents for the polymer being synthesized, based upon the total weight of the reaction medium. In most cases the reaction medium will contain less than 4% by weight solvents or virtually no solvents at all.

Temperatures at which the polymerization reaction is carried out can be varied over a wide range. Usually the temperature can be varied from extremely low temperatures such as −60° C. up to high temperatures such as 150° C. or higher. Thus, the temperature is not a critical factor of the invention. It is generally preferred, however, to conduct the reaction at a temperature in the range of from about 10° C. to about 90° C. The pressure at which the polymerization is carried out can also be varied over a wide range. The reaction can be conducted at atmospheric pressure or, if desired, it can be carried out at sub-atmospheric or super-atmospheric pressure. Generally, a satisfactory polymerization is obtained when the reaction is carried out at about autogenous pressure, developed by the reactants under the operating conditions used.

The vinyl halides can be utilized as molecular weight regulators in accordance with the teachings of U.S. Pat. No. 4,663, 405. The teachings of U.S. Pat. No. 4,633,405 are incorporated herein by reference in their entirety. Some representative examples of vinyl halides that can be used include vinyl fluoride, vinyl chloride, vinyl bromide and vinyl iodide. Vinyl bromide, vinyl chloride and vinyl iodide are preferred. Generally, vinyl chloride and vinyl bromide are the most preferred.

The amount of vinyl halide utilized will vary with the molecular weight that is desired for the polymer being synthesized. Naturally, the use of greater quantities of the vinyl halide results in the production of a polymer having lower molecular weights. As a general rule, from about 0.05 to 10 phm (parts per hundred parts of monomer) of a vinyl halide will be utilized. In most cases from 0.1 phm to 2.5 phm of a vinyl halide will be present during the polymerization. Persons skilled in the art will be able to easily ascertain the amount of vinyl halide needed in order to produce a polyisoprene having the desired molecular weight.

Figure 15:
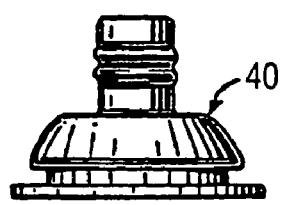
FIG. 15 is a side elevational view of a standard Playtex nipple.

Neodymium polyisoprene rubber can be used advantageously in manufacturing nipples for baby bottles. For example, baby bottle nipples that are comprised of neodymium polyisoprene rubber which have conventional designs can be manufactured using standard techniques. Such designs include the standard Playtex nipple 40 shown in FIG. 15 and the standard Evenflo nipple 41 shown in FIG. 16. Nipples for baby bottles of the design disclosed in U.S. Pat. No. 6,253, 935 can also be manufactured utilizing neodymium polyisoprene rubber. The teachings of U.S. Pat. No. 6,253,935 are accordingly incorporated by reference herein in their entirety. A nipple of the design disclosed in U.S. Pat. No. 6,253,935 is shown in FIG. 1.

Figure 1:
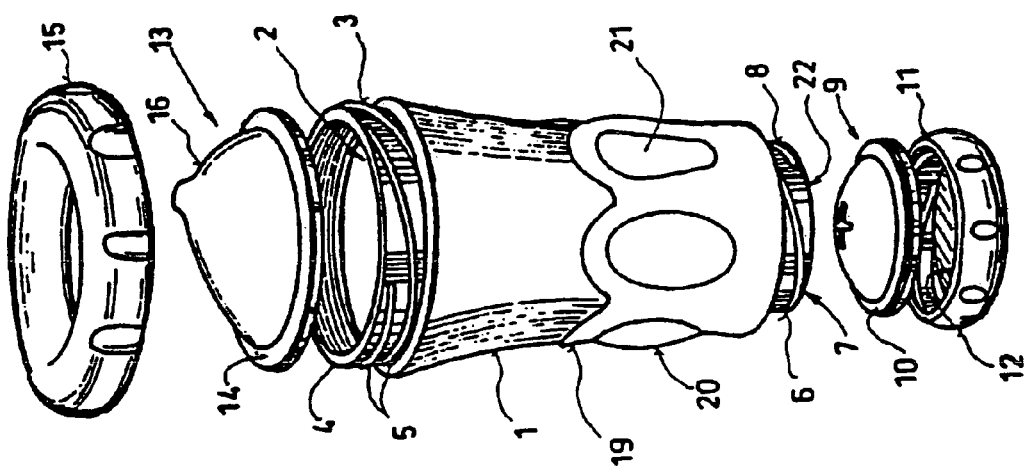
FIG. 1 is an exploded perspective view of one embodiment of a baby's bottle and nipple combination.
Figure 5:
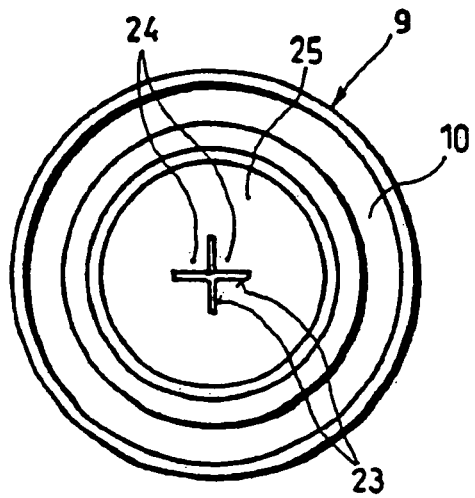
FIGS. 5 to 8 are plan views and side elevations of the parts forming the bottom of the bottle, i.e. a check-valve body and a fastener ring.

A baby's bottle according to FIG. 1 comprises a substantially cylindrical, tubular wall body 1. This body 1 may be formed by a clear plastic material, e.g. by a polycarbonate or an oriented polypropylene and is divergent in upward direction where it defines an opening 2 which is surrounded by a collar-like edge projection 3. This projection 3 has a, relative small, front edge surface 4 and a thread 5 on its circumferential surface. In a similar way, the body 1 comprises a lower collar-like projection 6 having a lower, ring-shaped front surface 7 and an outer thread 8 on its circumferential surface. A valve insert 9 to be described below with reference to FIGS. 5 and 7 has an outer rim or flange 10, the upper surface of which is to be sealingly engaged by the lower front surface 7 of the collar 6. In order to press this rim 10 against the lower front surface 7, a bottom ring 11 to be described below with reference to FIGS. 6 and 8 has an inner thread to be screwed onto the outer thread 8 of projection 6. The bottom ring 11 has a substantially flat bottom wall 12 forming the base surface of the bottle when screwed on (FIG. 2).

Figure 3A:
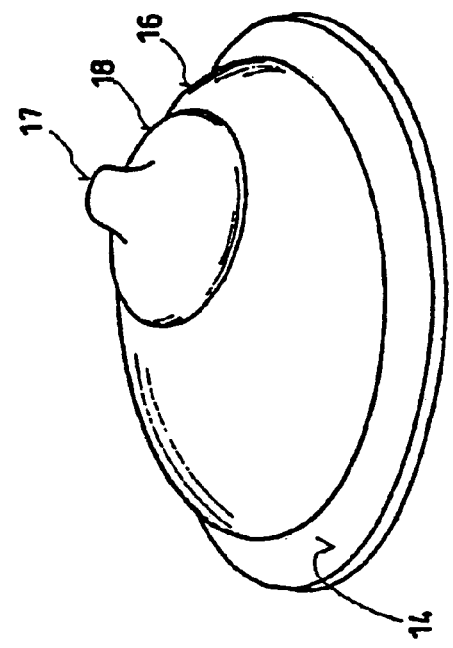
FIGS. 3a to 3c are different perspective views of the nipple shown in FIG. 1 and FIG. 2.
Figure 3B:
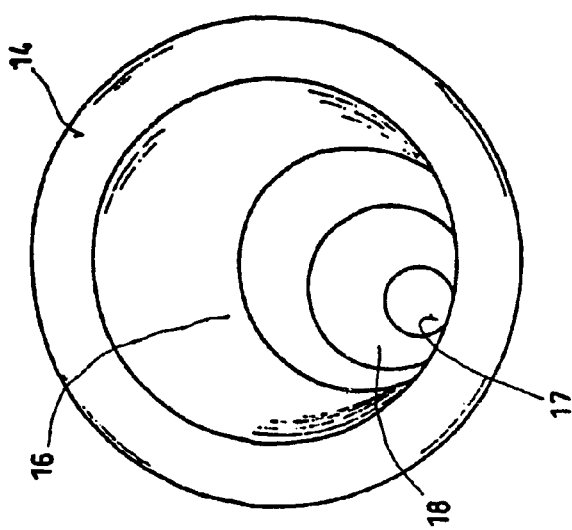
Figure 3C:
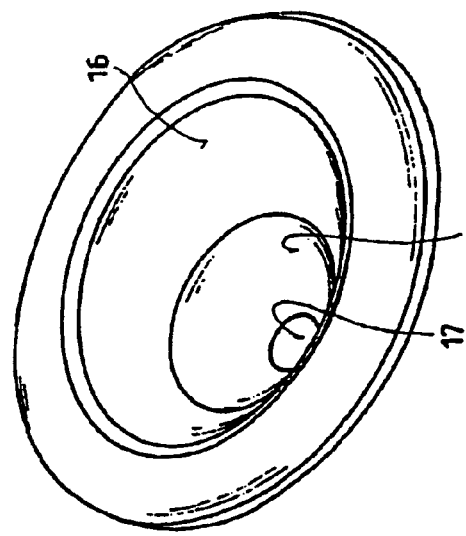
Figure 3D:
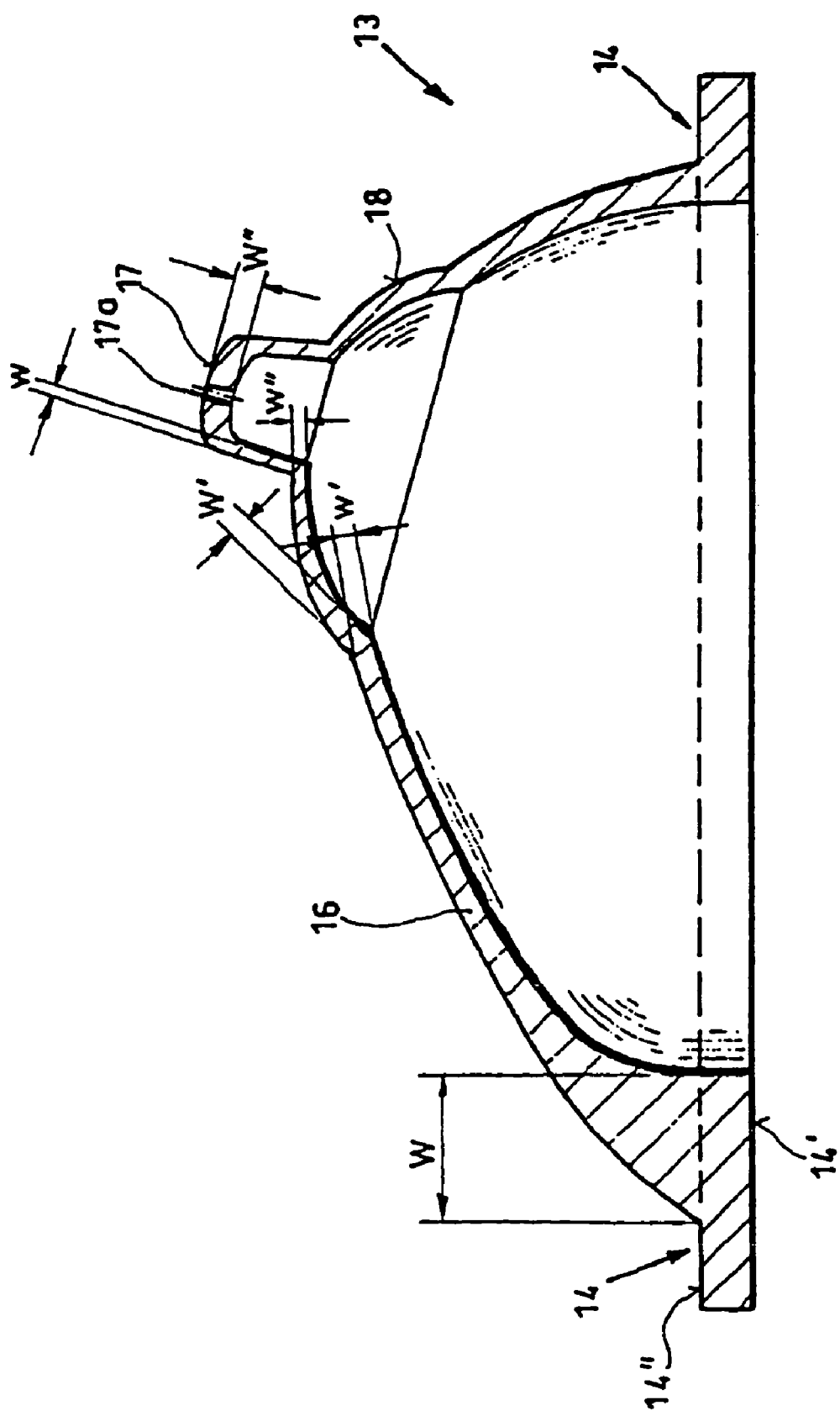
FIG. 3d shows an enlarged cross-section of the nipple shown in FIG. 1 and FIG. 2.

Similarly, a breast shaped nipple 13 has an outer sealing rim 14 including a lower sealing surface 14' and an upper sealing surface 14'' (FIG. 3*d*), the lower front surface of which engages the upper front surface 4. Above the sealing rim 14 rises the cupola of a breast forming wall 16. A fastening ring 15, e.g. of a substantially rigid plastic material, such as a polypropylene material, has an inner thread to be screwed onto the outer thread 5 of projection 3 so as to press the rim 14 sealingly against the upper front surface 4 of the wall body 1, while leaving an opening large enough to allow the breast wall 16 to pass through when assembled (FIG. 2). As can be seen in greater detail in FIGS. 3*a* to 3*d*, this breast wall ends up in a nipple portion 17, having at least one sucking hole in it, on the so-called areola portion 18 slightly bulging out. In a mother's breast, the milk glands are about in the region of the areola 18 that is seized by baby's palate, and there is a plurality of small channels which lead outwards. Similarly, the nipple portion 17 can be formed with several openings (only one opening 17*a* is shown in FIG. 3*d*), e.g. by laser boring. It is apparent that the divergence of the walls of body 1 widens the opening 2 so that a full-scale breast forming wall can be attached to the opening 2 which leads into the interior or cavity of the wall body 1. In this way, a baby can suck from a breast-shaped nipple that conforms in shape to the baby's palate.

Alternatively (if another shape of a bottle's nipple is chosen) or preferably in addition to the above-mentioned breast-shaped nipple 13, at least part of the nipple 13, i.e. at least the nipple portion 17 and/or the areola 18, but preferably the whole breast-shaped nipple 13 is made of neodymium polyisoprene rubber which is able to be stretched at least twice in dimension under a tension corresponding to a suction force of at least 130 mm Hg. This is based on findings what elasticity a human breast has, i.e. to be stretched at least about twice, at a suction force exerted ordinarily by a baby, i.e. at least 130, but in most cases no more than 200 mm Hg. The usual force is between 150 mm Hg and 200 mm Hg.

To enhance elastic deformation of the bottle nipple 13 in a manner quite similar to that of a human breast, it is suitable to confer it a wider wall thickness W (FIG. 3d) in the region of the lower sealing surface 14', and, generally, to decrease this thickness toward the nipple portion 17 so as to have a relative small thickness w in this region with exception of the top where the hole 17a is provided. Preferably, this decrease in thickness is made in steps, as shown in FIG. 3d. This means that each portion 16 and 18 of the bottle nipple 13 starts with its thickest section W or W', and ends in a thinner wall section w' or w" at its end. In this way, the thicker wall sections aid in avoiding collapsing. Collapsing can even be better avoided, if, for example, the thicker wall section W' is thicker, and in some cases significantly thicker, than the immediately adjoining (previous from bottom to top) thin wall section w'. From the asymmetry of the breast-shaped nipple 13 according to FIG. 3d, it will be clear that the thickness along the perimeter, say the thickness W or W' will normally be also asymmetric, but, if desired, can also be made symmetric in such a way that the thickness W, for example, is the same at right and at left of FIG. 3d. It is only the nipple portion 17 which has the thin wall thickness w at its lower end (for stretching) and its wider wall section W" at top. Certainly, it would be possible to make the rounding of portions 16 and 18 more flush, the areola portion 18 not bulging out in such a pronounced way. In such a case, it would be possible to have a wall which starts with thickness W and ends, at least substantially, with thickness w". In all cases, the thinner wall sections w, w' and w" enhance stretching of the respective regions. It is also clear according to FIG. 3d, that W>W', and, preferably, w'>w".

Figure 4:
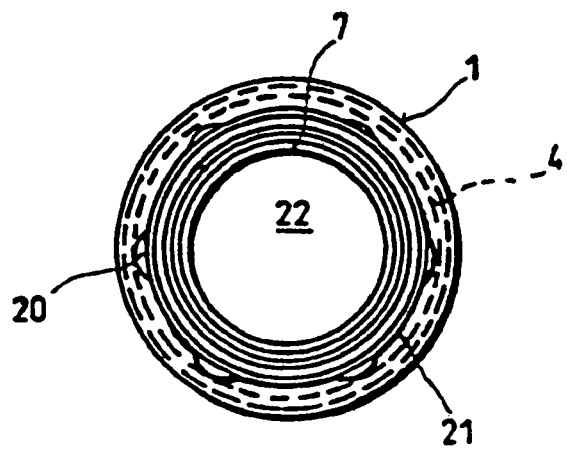
FIG. 4 is a bottom view according to arrow IV of FIG. 2.

Neodymium polyisoprene rubber can be used for forming an elastic grip ring on the outer surface of the transparent wall body 1. This grip ring 19 has either an annular or, as shown, a series of annularly distributed elastic bulges 20 distributed, according to FIG. 4, in a substantially hexagonal shape. There is at least one exception in that one bulge is omitted to provide an opening 21 (see FIGS. 1 and 2) through which the level of the liquid inside the bottle body 1 can be surveyed. If the bottle 1 is gripped below the elastic bulges 20 any slippage between the bottle and the hand will provoke that the bulges 20 are pressed from below and bulge more in upward direction, thus forming a stop against further slippage. Moreover, some babies like to grip the bottle and elastic feeling of the bulges comforts them. Therefore, it is not necessary to have only one ring of bulges, but more than one can also be provided over the axial length of the body 1. On the other hand, since this wall body 1 is made of a relative rigid material and is substantially cylindrical leaving and defining the opening 2 as well as a bottom opening 22 (FIG. 4), it is easy to clean because there are no recesses or projections inside and the inner surface is totally smooth.

When a baby sucks milk from a bottle, it exerts a certain sucking force. However, as liquid is removed, a vacuum or subpressure is created inside the bottle that balances more and more the suction force of the baby and prevents further sucking. U.S. Pat. No. 5,699,921, suggested the use of a check-valve which can be formed by elastic lips. In U.S. Pat. No. 5,699,921 two opposing lips are provided which open under a certain inner vacuum of the bottle to let air in the bottle. As particularly may be seen from FIG. 4 the two lips close tightly in the two directions they are bent, but the patent remains mute as to lateral sealing between the two lips. Moreover, arranging two lips in the manner shown and described there means that there are always some recesses and corners which can hardly kept clean.

The valve member 9 according to the present invention has a dome-like configuration formed by a dome wall 25 and having at least three, in the present embodiment four, crossing slots 23. It is contemplated that even more slots could be provided, such as six slots. More than six, however, may lead to sealing difficulties, because the flaps or tongues 24 defined by the slots 23 become weaker when more slots are provided and tend to engage the edge of the adjacent flap less reliably. In any case, due to the fact that the dome wall 25 bulges upwards, the flaps 24 are held tightly together as long as a positive force, such as the weight of the liquid, presses them downwards. However, they open easily as soon as there is a negative pressure inside the bottle 1. This elasticity is a reason why it is preferred to use the same material as is used for the nipple 13.

Figure 6:
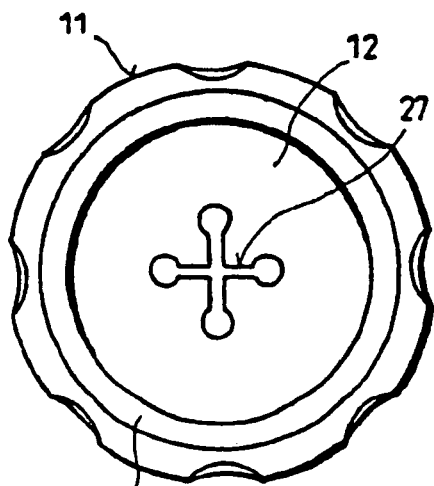
Figure 7:
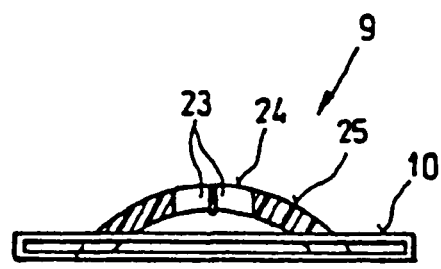
Figure 8:
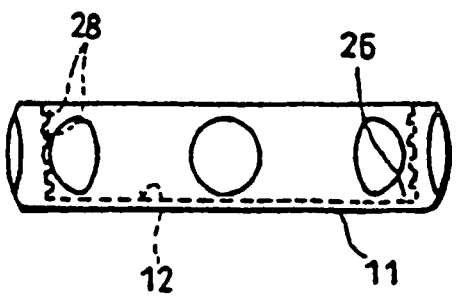
Figure 9:
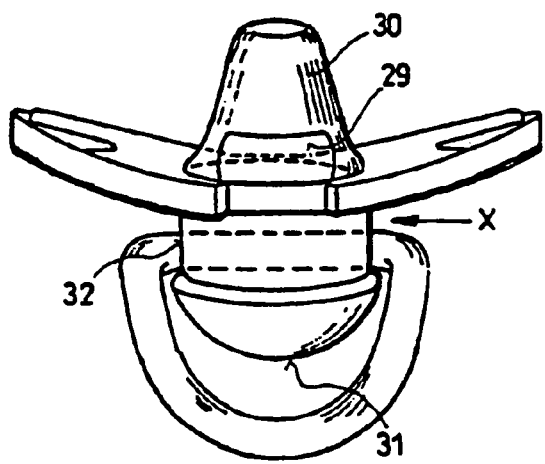
FIGS. 9 to 12 illustrate a pacifier in a front view, a side view, partly in cross-section, corresponding to arrow X of FIG. 9, and two perspective views.

As has been mentioned previously, the upper surface of the sealing rim 10 is pressed against the lower front surface 7 (FIGS. 1 and 4) of the cylindrical projection 6. This is done by the bottom ring 11 and its bottom wall 12. As shown in FIG. 6 and in FIG. 8 in dotted lines, the bottom wall 12 may have an annular step 26 the upper surface of which forms a sealing surface which presses against the lower surface of the rim 10 (FIG. 7). This, however, is not necessary, and the bottom wall 12 can be flat also in the interior of the bottom ring 11. In order to allow access of air to the valve member 9 and its slots 23, the bottom wall 12 has a cut-out 27 (FIG. 6), but it should be understood that neither the shape of such cut-out is critical nor where it is arranged. Access of air could also be provided by any opening or channel and could likewise be formed in the peripheral wall of the bottom ring 11. As is indicated in dotted lines, the inner peripheral wall surface of this ring 11 is provided with a thread 28 which is to engage the outer thread 8 of projection 6 (FIG. 1).

Figure 10:
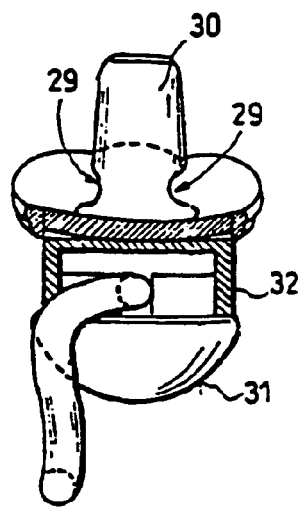
Figure 11:
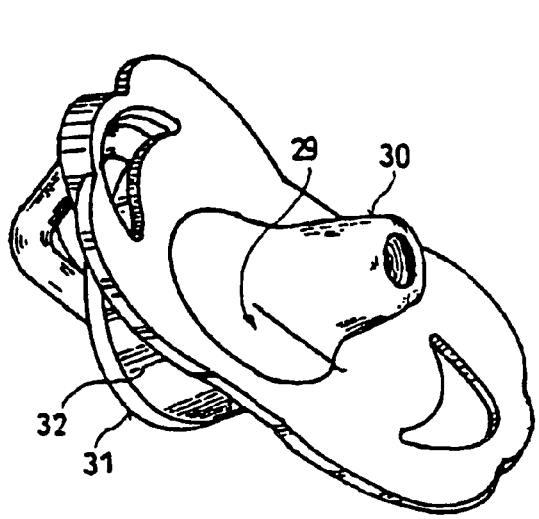
Figure 12:
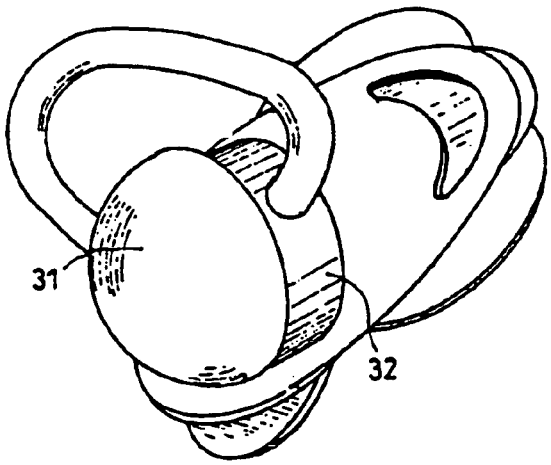

It has been mentioned above that a baby uses a special sucking technique when breastfed. It is useful not to accustom a baby to a different technique when sucking on a pacifier. Therefore, a pacifier as depicted in FIGS. 9 to 12 can also be manufactured utilizing neodymium polyisoprene rubber. As in the case of the bulges 20, a pacifier's nipple portion may be massive or full rather than hollow as it is the case with customary pacifiers. Moreover, FIG. 10 shows that it is preferred to have at least one recess 29 behind a freely projecting head portion 30, the recess 29 facilitating retaining the pacifier in the baby's mouth. This head portion, if made from one of the materials mentioned above can be stretched at least twice when the baby sucks it in, thus imitating the properties of a human breast nipple. In this case, it could be solid or full material that forms the head portion 30.

Alternatively, it would be possible to provide a hole in the free end of the head portion and to provide a cavity inside the head portion which communicates with the hole. In this way, health promoting substances could be filled into the cavity, e.g. by making a hat-shaped end portion 31 screwable on a cylinder 32 to provide access to such a cavity.

Figure 14:
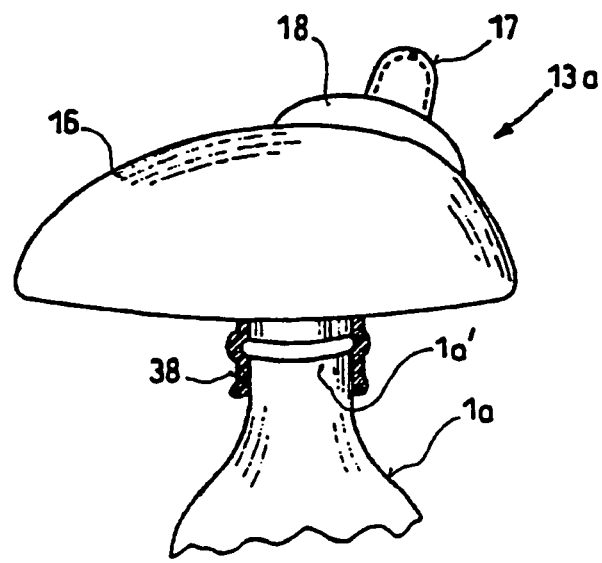
FIG. 14 shows an alternative combination of a breast-shaped nipple and the upper neck end of a baby's bottle.
Figure 13:
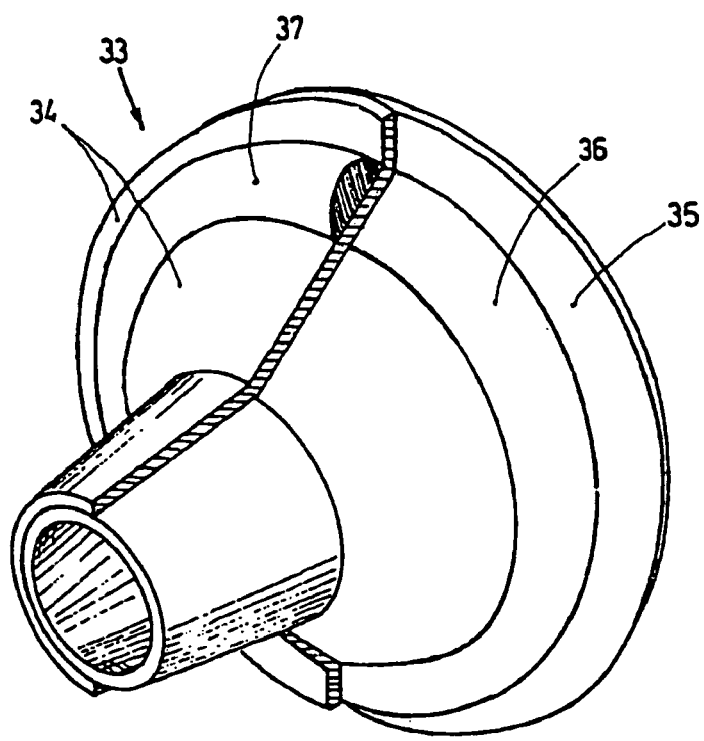
FIG. 13 represents a perspective view, partially in cross-section, of a breast hood formed according to the invention.

FIG. 13 shows a layered breast hood 33 comprising a relative hard and smooth outer layer 34, e.g. of a polycarbonate, and an inner layer 35 that is comprised of neodymium polyisoprene rubber. The advantage of such an inner layer 35 resides in its elasticity, on the one hand, and its characteristics similar to human skin, thus giving a good feeling. Preferably, the inner layer 35 comprises a bulge 36 protruding into the interior of the hood 33. This bulge needs not necessarily to have a continuous annular shape as shown and preferred, but can be formed by a series of protrusions, preferably arranged as a ring. Furthermore, it may be seen that the annular bulge 36 is near the widened open end of the hood 33, as is preferred. However, it could be arranged more inwardly, say about half way of the conical part of the hood 33. The reason is that such bulge may have two functions. On the one hand, it seals the hood 33 against the female breast, while, on the other hand, exerting a massage effect onto the skin (similar to sucking of a baby) which is enhanced by the particular elasticity of the material. In order to make this massage effect more similar to a baby's sucking, the annular bulge 36 can be arranged more inwardly so that it imitates the baby's mouth surrounding the portion 18 (see FIGS. 1, 2 and 14). An outer bulge 37 may surround the outer layer 34, but in this case the choice of a soft, resilient material is not critical, since it serves only to facilitating gripping of the hood 33. This outer bulge 37 can either be slipped over the outer layer 34 (which may have a groove for receiving the base of the bulge 37) or can be co-injection molded as will preferably be the inner layer 35. It is clear that the hood 33 may comprise more than two layers, but in any case the inner layer should be structured as described above. FIG. 14 shows an alternative to FIGS. 1 to 3c where, although the bottle nipple is breast-shaped as shown, it fits to a customary baby's bottle 1a with a relative narrow neck portion 1a' (only the upper part is illustrated). To this end, the lower surface of the breast-shaped bottle nipple 13a extends inwardly to an elastic connection piece 38 (of a size as in available bottle nipples) which may be drawn over the neck portion 1a'. The advantage of this modification is that no special bottle is necessary, while some drawback may be seen in the fact that the relative large breast-shaped upper portion is more unstable in position.

Figure 16:
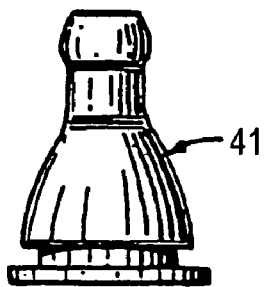
FIG. 16 is a side elevational view of a standard Evenflo nipple.
Figure 17:
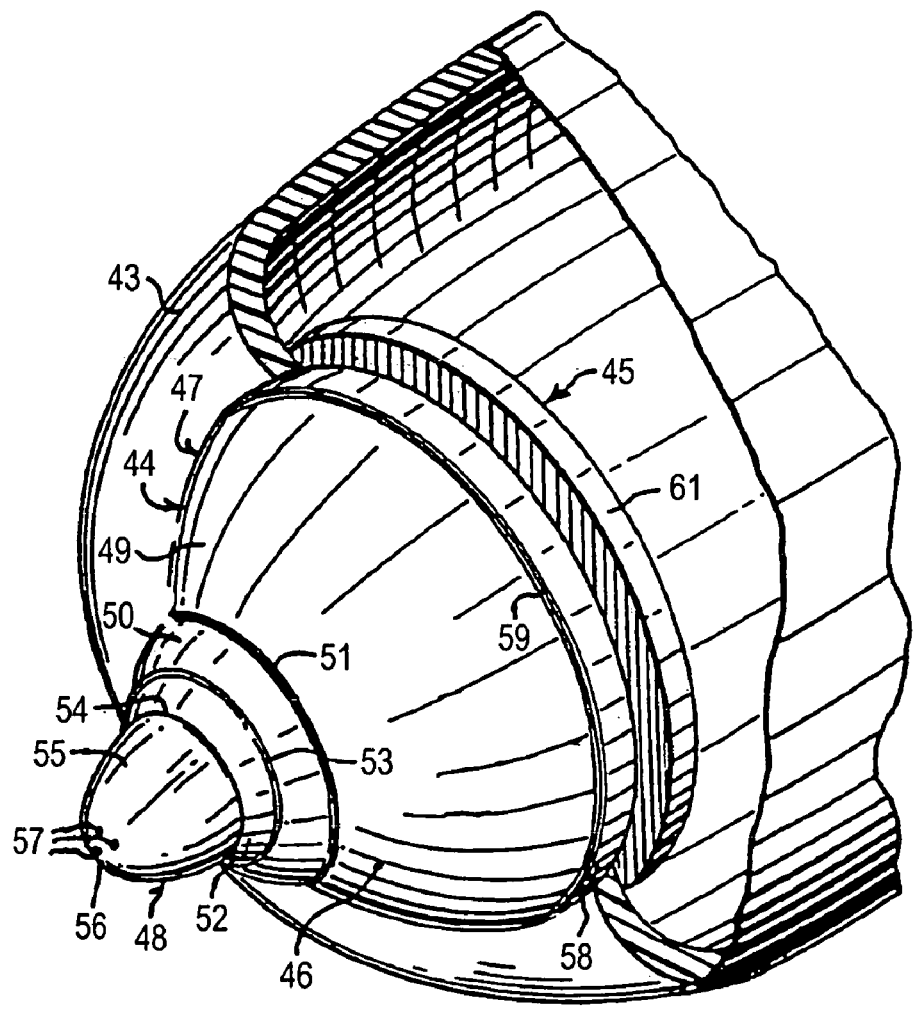
FIG. 17 is a perspective view of the nipple of U.S. Pat. No. 5,653,732 and associated cap, which is broken away.

Baby bottle nipples of the design disclosed in U.S. Pat. No. 5,653,732 can also be manufactured using neodymium polyisoprene rubber. The teachings of U.S. Pat. No. 5,653,732 are incorporated by reference herein in their entirety. FIGS. 16 and 17 show baby bottle nipples of the design disclosed by U.S. Pat. No. 5,653,732.

Figure 18:
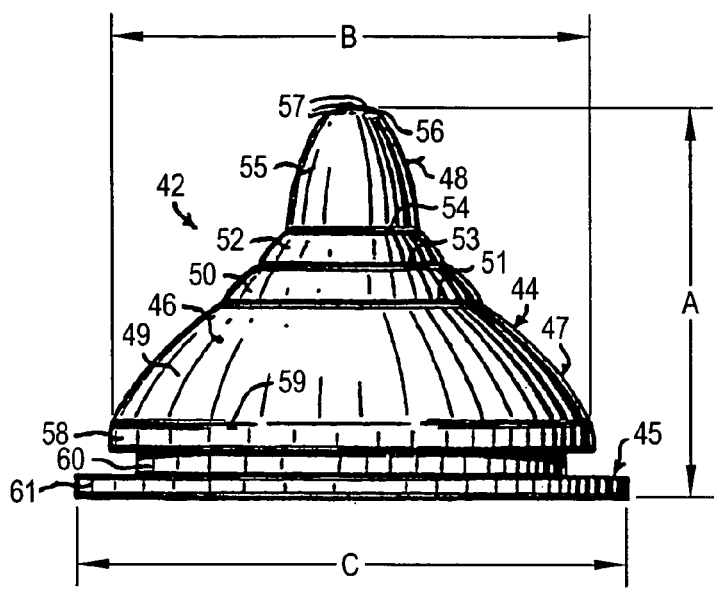
FIG. 18 is a side elevational view of the nipple of U.S. Pat. No. 5,653,732 per se.
Figure 19:
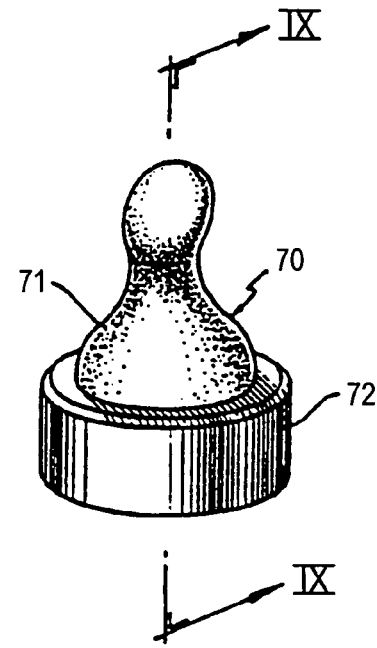
FIG. 19 is a perspective view of a nipple incorporating the principles of U.S. Pat. No. 4,676,386.

FIGS. 17 and 18 illustrate a natural formed nipple 42 for a baby bottle, having an externally threaded neck and an internally threaded cap with a central aperture 61. The nipple 42 comprises a mouthpiece 44 constructed as close as possible to the shape of a female human breast. A structure 45 is for securing the mouthpiece 44 at the central aperture 61 in the internally threaded cap 43 to a top edge of the externally threaded neck of the baby bottle in a waterproof sealed manner. When a baby suckles on the mouthpiece 44, it makes the weaning process easier for the baby.

The mouthpiece 44 and the securing structure 45 are integral and fabricated out of neodymium polyisoprene rubber 46. The mouthpiece 44 includes a dome-shaped crown 47 and a tip 48 extending upwardly from the dome-shaped crown 47. The dome-shaped crown 47 consists of a lower segment 49 having a large curved outer surface. An intermediate segment 50 has a smaller curved outer surface than the lower segment 49. A first annular ridge 51 is between the lower segment 49 and the intermediate segment 50. An upper segment 52 has a smaller curved outer surface than the intermediate segment 50. A second annular ridge 53 is between the intermediate segment 50 and the upper segment 52. A third annular ridge 54 is between the upper segment 52 and the tip 48.

The tip 48 is a small conical protuberance 55 on the third annular ridge 54, so as to simulate a female human teat. The small conical protuberance 55 contains a curved apex surface 56, having three small holes 57 therethrough, to allow any liquid within the baby bottle to exit therefrom when the baby suckles.

The securing structure 45 includes an annular base 58 at a bottom edge 59 of the lower segment 49 of the dome-shaped crown 47, being of the same diameter as the bottom edge 59 of the lower segment 49. An annular recessed collar 60 under the annular base 58 is of a smaller diameter than the annular base 58 and of the same diameter as the central aperture 61 in the cap. An annular flange 61 under the annular recessed collar 60 is of a larger diameter than the annular base 58 and the annular recessed collar 60 and of the same size as the internal diameter in the cap. The annular base 58 can be forced through the central aperture 61 in the cap, while the annular flange 61 will be held between the cap and the top edge of the externally threaded neck of the baby bottle.

The height from a bottom surface of the annular flange 61 to the curved apex surface 56 of the small conical protuberance 55 is approximately, but not limited to, 1.5 inches. The diameter of the annular base 58, as indicated by letter B in FIG. 18, is approximately, but not limited to, 1⅞ inches. The diameter of the annular flange 61, as indicated by letter C in FIG. 18, is approximately, but not limited to, 2⅛ inches.

Neodymium polyisoprene rubber can also be used in manufacturing baby bottle nipples and pacifiers of the designs disclosed in U.S. Pat. No. 4,676,386. The teachings of United States Patent are accordingly incorporated by reference herein in their entirety.

The nipple design of United States Patent is illustrated in FIGS. 19-22, which best show the general features of the nipple. It can be seen that the nipple, indicated generally by the reference numeral 70, consists of a mouth portion 71 and a base or cap portion 72. The mouth portion 71 is formed of neodymium polyisoprene rubber. The cap portion 72 is formed around the mouth portion, and is formed of a polymer having a relatively low melting temperature. In a preferred embodiment, the elastomer is liquid silicone rubber.

Figure 20:
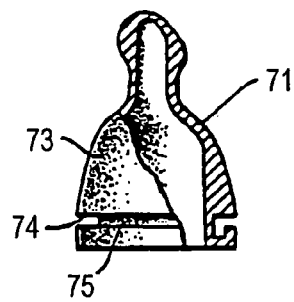
FIG. 20 is a front elevational view of the nipple of U.S. Pat. No. 4,676,386 with portions broken away.
Figure 21:
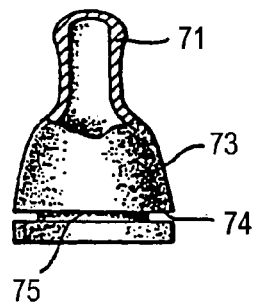
FIG. 21 is a side elevational view of the nipple of U.S. Pat. No. 4,676,386 with portions broken away.
Figure 22:
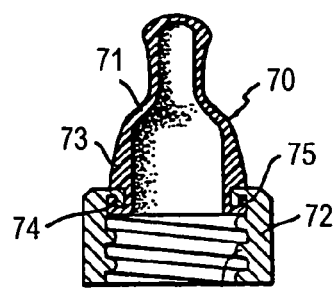
FIG. 22 is a vertical sectional view of the nipple taken on the line IV-IV of FIG. 19.

As is evident in FIGS. 20 and 21, the mouth portion 71 has a lower skirt 73 formed with an external groove 74 into which the cap portion is locked. The groove extends entirely around the skirt, has an L-shaped cross-section, and has a textured surface 75.

Neodymium polyisoprene rubber can also be used be advantageously employed in manufacturing ear and nasal syringes. For instance, ear syringes and nasal syringes having conventional designs can be manufactured using neodymium polyisoprene rubber. U.S. Pat. No. 5,114,415 discloses an apparatus for removing fluid secretions from a patient's upper airway which includes a power driven suction generator connected to one end of a flexible tube and a nozzle removably connected to the other end of the tube. The nozzle is constructed to be manually positioned and maintained in an operative position adjacent oropharynx and nasopharynx openings and is proportioned relative to such openings to permit not more than minimal insertion of the nozzle through such openings. In one embodiment of U.S. Pat. No. 5,114,415, the nozzle is constructed of rigid material and is adapted to be utilized as a nozzle for a manually operated nose syringe. In another embodiment, the nozzle is constructed of relatively soft rubber-like material and is essentially of the same gradually tapered shape as the nozzle portion of a manually operated ear syringe. Beneficial results can be realized by employing neodymium polyisoprene rubber as the relatively soft rubber-like material in the nozzle.

An ear syringe of the type described in U.S. Pat. No. 5,114,415 can be manufactured utilizing neodymium polyisoprene rubber as the nozzle means. The teachings of U.S. Pat. No. 5,114,415 are incorporated herein by reference with respect to the design of ear syringes. This invention accordingly discloses an apparatus for maintaining a patient's upper airway clear by removing fluid secretions through such patient's oropharynx and nasopharynx, said apparatus including: power driven first means for generating suction at an input port thereof; flexible connecting tube means having a first end operatively connected to said input port, and a second end remote from said first end; removable nozzle means operatively connected to said second end; said nozzle means being operatively constructed to be operatively positioned and maintained manually at oropharynx and nasopharynx openings for suction removal of fluid secretions therethrough; said nozzle means being operatively constructed and proportioned relative to such openings to permit no more than minimal insertion of the nozzle means through such openings; and said nozzle means including a flange having at least one aperture therethrough, said flange being located adjacent said removable nozzle means for partially blocking air flow into and out of said oropharynx and nasopharynx openings during said suction removal, wherein the nozzle means is comprised of neodymium polyisoprene rubber.

Neodymium polyisoprene rubber can also be utilized in manufacturing ear syringes of the type described in U.S. Pat. No. 4,258,714, the teachings of which are herein incorporated by reference. This invention accordingly discloses an ear syringe having a built-in pressure regulator valve to control the discharge velocity of fluid issuing from the nozzle of the syringe, regardless of the amount of pressure applied on the bulb of the syringe, to prevent pain in the ear of a user, or possible damage to the ear as a result of squeezing the bulb too hard, or applying a sudden excessive pressure to the bulb. This invention further discloses an ear syringe including a compressible bulb and a nozzle, a restriction between the interior of the bulb and the nozzle, said nozzle having means comprising an expansion chamber which reduces the velocity of fluid discharged from the bulb through the nozzle, said expansion chamber being open adjacent to the discharge end of the nozzle, an opening in said bulb, said nozzle mounted in said opening, said restriction including a valve at the inner end of said nozzle mounted at least partially within said opening, said valve including an inner flap member movable between an open fill position and a closed discharge position, and an opening of predetermined size through the flap member effective in the closed position to restrict fluid flow to said expansion chamber and to reduce the velocity of fluid discharged through the open end of the nozzle, wherein the valve is comprised of neodymium polyisoprene rubber.

Figure 23:
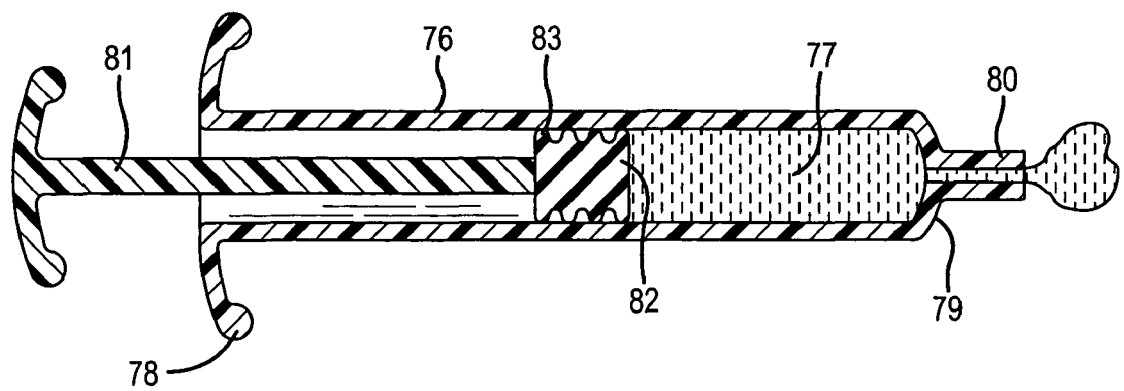
FIG. 23 is a cross-sectional view of a syringe equipped with a plunger having a syringe plunger tip.

Neodymium polyisoprene rubber can also be utilized in manufacturing syringes, such as those used in medical applications. Such a syringe is illustrated in FIG. 23. Such syringes are comprised of a barrel 76 having a fluid chamber 77, a proximal end 78, a distal end 79 and an elongated tip 80 extending from said distal end 79 having a passageway therethrough in fluid communication with said chamber 77, and an elongated plunger rod 81 including a stopper 82 slidably positioned in fluid-tight engagement with an inside surface of said chamber for drawing fluid into and out of said chamber by movement of said plunger relative to said barrel, wherein the stopper is comprised of neodymium polyisoprene rubber. It is normally preferred for the stopper 82 to be of a design that includes ribs 83 that facilitate movement of the plunger 81 through the barrel 76.

The syringes of this invention include those having the design described in U.S. Pat. No. 6,217,550, the teachings of which are herein incorporated by reference. This invention accordingly discloses a syringe comprising: a barrel having a fluid chamber, a proximal end, a distal end and an elongated tip extending from said distal end having a passageway therethrough in fluid communication with said chamber; and a plunger including an elongated plunger rod having a longitudinal axis, a proximal portion and a distal portion connected by a breakable connection, one of said proximal portion and said distal portion including an axial projection having a plurality of transverse protuberances projecting therefrom, said protuberances being connected to the other of said proximal portion and said distal portion, said breakable connection being on said protuberances, said distal portion including a stopper slidably positioned in fluid-tight engagement with an inside surface of said chamber for drawing fluid into and out of said chamber by movement of said plunger relative to said barrel, wherein the stopper is comprised of neodymium polyisoprene rubber, said breakable connection being strong enough to hold said proximal portion and said distal portion together during normal use of said syringe and breakable upon application of an additional force applied to said proximal portion along said longitudinal axis.

The syringes of this invention can also be of the design described in U.S. Pat. No. 4,030,498, the teachings of which are incorporated herein by reference. Such a syringe is comprised of a barrel defining a bore and having a discharge portion, and a plunger extending into said bore and movable therewithin, in combination with an inner sealing means carried by said plunger and movable axially within said bore in an area proximate to said discharge portion for substantially preventing leakage of medicament or other biologic fluid contained in the space forward of said inner sealing means adjacent said discharge portion; outer sealing means carried by said plunger, said outer sealing means being spaced axially from said inner sealing means and movable axially within said bore in an area behind the travel area of said inner sealing means; said plunger having an axial length within the bore of more than one-half of the functional length of the bore void of sealing rings; and means for preventing said outer sealing means from moving in the area in which said inner sealing means travels, wherein said sealing means is comprised of neodymium polyisoprene rubber.

A piston for a syringe of the type described in U.S. Pat. No. 4,180,069 can be manufactured utilizing neodymium polyisoprene rubber. The teachings of U.S. Pat. No. 4,180,069 are incorporated herein by reference with respect to a piston used for a syringe. This invention accordingly discloses a piston made of a flexible material adapted to be assembled to a plunger rod and being of generally cylindrical shape, said piston having a pocket extending inwardly from one inner axial end face thereof, said pocket being of a truncated Christmas tree configuration in cross section defining a series of pocket sections decreasing in cross wise dimension from the open throat end of the piston to define a series of circumferentially extending radially inwardly directed flexible lips between adjacent pocket sections, the conical wall of the innermost and outermost pocket sections being tapered at an included angle less than the angle of taper of the conical wall of the intermediate pocket sections, wherein said piston is comprised of neodymium polyisoprene rubber.

Neodymium polyisoprene rubber can also be advantageously employed in manufacturing a syringe assembly of the type disclosed in U.S. Pat. No. 4,412,836. The teachings of United States Patent are accordingly incorporated by reference herein in their entirety. This invention discloses a plunger for a syringe made of a resilient material comprising a generally cylindrical body portion, a plurality of radial axially spaced ribs on its outer peripheral, a rupturable diaphragm spaced inwardly from opposite axial ends of the body portion, said diaphragm having a localized weakened area to minimize particle formations when the diaphragm ruptures, and also providing a more accurate control of force required to rupture the diaphragm consisting of a crescent-shaped membrane portion of thinner cross section than the remainder defined by the crescent and the circular trace of the diaphragm. Beneficial results can be realized by employing neodymium polyisoprene rubber as the resilient material of which the plunger is made.

An injection apparatus of the type described in U.S. Pat. No. 5,823,998 can be manufactured utilizing neodymium polyisoprene rubber. The teachings of U.S. Pat. No. 5,823,998 are incorporated herein by reference. This invention accordingly discloses an injection apparatus, comprising an ampule having a piston for sealing an agent in a syringe, comprising: piston rod means for pressing the piston of the ampule in an axial direction; an ampule holding part having an ampule insertion outer opening, having an original circumference, which opening is expanded circumferentially when the ampule is inserted into the opening and having an ampule insertion space for inserting the ampule thereinto, wherein the outer opening is restored to its original circumference after the ampule is inserted into the ampule insertion space, so that the ampule is held by the ampule holding part temporarily; and ampule gripping means for gripping the ampule and preventing axial movement thereof wherein a concave part is formed on a peripheral surface of the piston rod, wherein the concave part comprises a bottom surface generally parallel with an inner peripheral surface of the guide sleeve, a front step surface being provided on a front side of the bottom surface and extending from the bottom surface outwardly in a radial direction of the piston rod; and a rear step surface being provided on a rear side of the bottom surface and extending from the bottom surface outwardly in the radial direction of the piston rod, and wherein the piston rod means further comprises spring means for automatically returning the screw rod and the piston rod to the initial position when a force for pushing in the screw rod and the piston rod is released, and a stopper member which is positioned in the concave of the piston rod, slides in contact with the bottom surface of the piston rod and the inner peripheral surface of the guide sleeve with a predetermined frictional force, moves together with the piston rod with the stopper member in contact with the rear step surface of the piston rod when the piston rod is pushed in, and stops the movement of the piston rod with the stopper member in contact with the front step surface of the piston rod when the piston rod is returned by the spring means, wherein a frictional force between the stopper member and the bottom surface of the piston rod is smaller than an automatic return force of the spring means; and a frictional force between the stopper member and the inner peripheral surface of the guide sleeve is greater than the automatic return force of the spring means, wherein the stopper member is comprised of neodymium polyisoprene rubber.

Neodymium polyisoprene rubber can also be utilized in manufacturing syringe assemblies of the type described in U.S. Pat. No. 4,405,317, the teachings of which are herein incorporated by reference. This invention accordingly discloses a syringe assembly comprising an outer barrel for a powder medicament, an inner barrel telescopically mounted in the outer barrel for diluent, seal means isolating the powder and diluent compartments comprising a plug member made of a resilient material sealingly engaging in the discharge opening of the inner barrel, plunger means mounted on the discharge end of the inner barrel including a hollow plug chamber closed at one end remote from the discharge end of the inner barrel by a wall having a plurality of discharge openings therein, said plug member including a pintle projecting from one axial end face thereof of said plug member of a diameter less than the body portion of said plug member and greater than the discharge openings in said plunger end wall, said plug member adapted upon pressure buildup in the inner barrel to be displaced axially outwardly into said plug chamber to permit flow of diluent from the inner barrel to the powder compartment, wherein the plug member and/or plunger are comprised of neodymium polyisoprene rubber.

Neodymium polyisoprene rubber can also be advantageously employed in manufacturing a syringe system of the type disclosed in U.S. Pat. No. 5,876,372. The teachings of U.S. Pat. No. 5,876,372 are accordingly incorporated by reference herein. This invention discloses a syringe mixing and delivery system comprising a first barrel having an open end and an opposite delivery end defining a delivery passage; a reciprocable stopper sealingly disposed in said first barrel to define a first chamber between said delivery passage and said reciprocable stopper for containing a first constituent in said first chamber; a second barrel that is sized to be disposed in said first barrel and that has an open end and an opposite discharge end defining a discharge passage; a slidable plunger sealingly disposed within said second barrel to define a second chamber between said discharge passage and said slidable plunger for containing a liquid second constituent in said second chamber; and fluid transfer connector means for operatively connecting said second barrel with said reciprocable stopper to permit flow of said liquid second constituent through said stopper from said second chamber to said first chamber to mix with said first constituent when said second barrel discharge end and plunger are moved closer together whereby subsequent movement of said second barrel and reciprocable stopper together toward said delivery passage of said first barrel expresses the mixed constituents out of said first chamber through said delivery passage, wherein said reciprocable stopper and plunger are comprised of neodymium polyisoprene rubber.

A pre-filled syringe drug delivery system of the type described in U.S. Pat. No. 5,785,682 can be manufactured utilizing neodymium polyisoprene rubber as the reciprocable stopper. The teachings of U.S. Pat. No. 5,785,682 are incorporated herein by reference. This invention accordingly discloses a drug delivery system, comprising a first pre-filled syringe assembly comprising a first syringe barrel having an interior surface, an open end, and an opposite delivery end which defines a drug delivery passage; a reciprocable stopper slidably disposed within said first syringe barrel in sealing engagement therewith for defining an internal mixing chamber within said first syringe barrel in communication with said delivery passage; and a sterility maintenance sleeve extending from said reciprocable stopper toward said open end of said first syringe barrel, said sterility maintenance sleeve maintaining the sterility of the interior surface of said first syringe barrel; a second pre-filled syringe assembly comprising a second syringe barrel having a fluid discharge passage at one end thereof, said second syringe barrel being sized to be disposed within the sterility maintenance sleeve of said first syringe assembly a movable piston plunger positionable within said second syringe barrel to define a fluid chamber therewith in communication with said fluid discharge passage; and a liquid in the fluid chamber of said second syringe barrel; and said system further including fluid transfer connector means for providing fluid communication from the fluid chamber of said second syringe assembly to said internal mixing chamber of said first syringe assembly when said second syringe assembly is disposed within said sterility maintenance sleeve so that the liquid within said fluid chamber can be caused to flow through said fluid transfer connector means into said internal mixing chamber of said first syringe assembly by movement of said piston plunger toward said fluid discharge passage of said second syringe assembly and thereafter caused to flow from said mixing chamber of said first syringe assembly through said drug delivery passage by movement of said second syringe assembly together with said reciprocable stopper and said sterility maintenance sleeve toward the drug delivery passage of said first syringe assembly, said fluid transfer connector means includes means for regulating the flow of fluid through said reciprocable stopper, said reciprocable stopper has an outer side facing toward said open end of said first syringe barrel and an inner side facing toward said drug delivery passage, said means for regulating the flow of fluid through said reciprocable stopper comprises said reciprocable stopper having a resilient body with a longitudinal slit through the resilient body defining two normally closed resilient lips, and the resilient body of said reciprocable stopper is substantially hollow and includes an enlarged cavity and a smaller entrance passage; and said sterility maintenance sleeve further includes: an enlarged head for being received in said enlarged cavity un said enlarged cavity of said resilient body, a smaller neck for being received in said smaller entrance passage of said resilient body, and a radially extending support flange adjacent said smaller neck for axially supporting said reciprocable stopper outer side, wherein said reciprocable stopper is comprised of neodymium polyisoprene rubber.

Neodymium polyisoprene rubber can also be utilized in manufacturing syringe barrels of the type described in U.S. Pat. No. 5,779,668, the teachings of which are herein incorporated by reference. This invention accordingly discloses a syringe system comprising: a primary syringe barrel having a delivery end defining a delivery passage and an opposite end having an edge and a venting portion with an inner surface and a larger transverse cross section; a removable closure sealing the delivery passage of the primary syringe barrel to define a chamber for containing a medical solution; a plurality of longitudinal channels on the inner surface of the venting portion of the open end of said primary syringe barrel; a plurality of rib portions in the venting portion between said channels, said opposite end of said primary syringe barrel has a smooth portion along the inner surface between said edge and said rib portions; and a reciprocable stopper for slidably sealing said primary barrel wherein the reciprocable stopper has a first position abutting the channels of the inner surface of the venting portion to allow the medical solution to be lyophilized, and is then axially movable in the direction of the delivery passage to a second position to sealingly enclose the lyophilized drug within the sealed delivery end of the primary syringe barrel, wherein the penetrable portion of said reciprocable stopper is comprised of neodymium polyisoprene rubber.

Reusable syringes of the type described in U.S. Pat. No. 4,701,165 can be manufactured utilizing neodymium polyisoprene rubber as the plunger. The teachings of U.S. Pat. No. 4,701,165 are incorporated herein by reference. This invention accordingly discloses a push rod for a syringe, said push rod having a hole in its end, a first section of the hole being threaded near the entrance of the hole, a second section of the hole which is remote from the entrance having an internal diameter which is larger than the diameter of the first threaded section in order to form a clearance room at the inner end of said hole, a plunger having a stud with an interrupted thread, the outer end of said stud having a thread which meshes and mates with the thread in said first section and the inner end of said stud having a smooth perimeter with a diameter which is less than the diameter of said first section of said hole, whereby said smooth inner end of said stud moves freely within the threaded section near the entrance of said hole, wherein said plunger is comprised of neodymium polyisoprene rubber.

Neodymium polyisoprene rubber can also be utilized in manufacturing the syringe and tip cap assembly of the type described in U.S. Pat. No. 6,196,998, the teachings of which are herein incorporated by reference. This invention accordingly discloses a syringe with a syringe barrel having a substance receiving chamber and a distally projecting tip with a fluid passage extending therethrough and a tip cap assembly attached to the projecting tip, said tip cap assembly comprising a collar concentrically surrounding the tip, the collar including an array of internal threads for threadingly engaging a needle hub; a resilient inner cap having opposed proximal and distal ends, said proximal end defining a tip engaging portion for sealingly engaging the tip to seal a substance contained in the chamber of said syringe barrel; a rigid outer cap securely engaged around at least a portion of said inner cap, said outer cap having a sleeve engageable with the collar such that said outer cap securely and releasably retains said collar therein and said inner cap in sealing engaged with the tip; and tamper indicator means provided on said sleeve of said outer cap for indicating separation of said outer cap from said collar and said tamper indictor means including a plurality of frangible portions separating said outer cap into a proximal portion and a distal portion, with the proximal portion surrounding said collar, wherein said resilient inner cap is comprised of neodymium polyisoprene rubber.

Reusable syringes of the type described in U.S. Pat. No. 4,701,165 can be manufactured utilizing neodymium polyisoprene rubber as the plunger. The teachings of U.S. Pat. No. 4,701,165 are incorporated herein by reference. This invention accordingly discloses a syringe comprising an elongate barrel having a proximal end and a distal end, with at least one chamber formed between the ends; a plunger sealably disposed within said barrel and movable with respect thereto; sealing means sealably disposed approximate said distal end of said barrel; at least one substance sensitive to pH shift prefilled in said chamber; and said barrel being made of a low extractable ion glass whereby over an extended period of time, the pH of said substance situated in said chamber of said barrel is maintained within a desired range, wherein said plunger is comprised of neodymium polyisoprene rubber. A pre-filled version of such a syringe can also be manufactured utilizing neodymium polyisoprene rubber. Such a prefillable syringe comprising: a generally cylindrical barrel in the shape of a hollow cylinder made of a low extractable ion glass with an open front end; a plunger, sealably disposed within said barrel and movable with respect thereto; a cylindrical stopper, having an outside diameter which is slightly larger than an inside diameter of the barrel and including means which seal the front end of the barrel; and a needle holder, including a collar which is attached in sealing relationship to the front end of the barrel, a neck for sealable attachment to an injection needle, the neck having a rear face which includes an aperture which functions to conduct fluid to the needle, and a hollow, internal shaft having a rear end which is sealably connected to the collar and a front end which is sealably connected to the neck; wherein the inner walls of the shaft and the rear face of the neck define one or more slots which extend from the rear end of the shaft to the aperture, wherein the cylindrical stopper comprises neodymium polyisoprene rubber.

Stoppers for sealing infusion bottles of the type described in U.S. Pat. No. 6,241,112 can be manufactured utilizing neodymium polyisoprene rubber. The teachings of U.S. Pat. No. 6,241,112 are incorporated herein by reference. This invention accordingly discloses a stopper for sealing infusion bottles containing pharmaceutical liquids, which stopper has a collar, which projects into the opening in the neck of the container and has a diameter greater than the neck opening; an edge, which rests on the neck of the container; and a puncture area, enclosed by the edge and the collar, the stopper being held on the neck of the container by a protective cap of metal or plastic, characterized in that the top surface of the puncture area is lower than the top surface of the edge, and in that the bottom surface of the stopper inside the collar as well as the top surface of the puncture area are relatively flat, and in that a transverse plane formed by end surface of container neck passes through approximately the center of the vertical thickness of the puncture area, and wherein the length of said collar is generally the same as the cross sectional thickness of the puncture area, the puncture area having a predetermined elasticity and flexibility with respect to the edge and the collar whereby after the stopper has been inserted into the neck of container, the puncture area bulges slightly outward and remains in that position until the puncture needle of an infusion kit has been inserted into the stopper, and in that the puncture area bulges down into neck of the container when being pierced by the puncture needle and remains in this position as long as the puncture needle is inserted into the stopper, wherein the puncture area of the stopper is made of neodymium polyisoprene rubber.

Neodymium polyisoprene rubber can also be used in elastic bands for face masks, leg bands for disposable diapers, medical fabric goods, hose nozzles, chew toys, grips for golf club shafts, shovel handles, handles for sports equipment and manual and electric tools, dental tools, rubber gloves, lyophilization stoppers and closures, protective gloves, condoms, tourniquets, dental dams, closures for serum vials, sleeve stoppers, needle guards, and medical tubing.

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLES

Materials.—Isoprene was supplied by The Goodyear Tire & Rubber Co, and was freshly distilled and degassed with nitrogen prior to use. Hexane was supplied from Ashland Chemicals and purified by passing over an activated bed of silica gel under a dry nitrogen atmosphere. Neodymium versatate solutions were provided by Rhodia Rare Earths Inc. and were used as received. Triisobutylaluminum (TIBA), diisobutyl-aluminum hydride (DIBAL), diethylaluminum chloride (DEAC), and diisobutyl-aluminum chloride (DIBAC) were all supplied by Albemarle Corp. as 20-25 weight percent solutions in hexane. Titanium polyisoprene under the trade name of Natsyn was supplied by The Goodyear Tire and Rubber Company. Lithium polyisoprene was provided as Cariflex 307 from Shell Chemicals.

Polymerizations.—Small scale batch polymerizations were carried out in oven dried glass bottles sealed with perforated metal screw caps containing a rubber gasket and a Teflon liner. Premix (12 to 18 weight percent isoprene in hexane) was charged into each bottle after it was first passed through a bed of silica gel under a nitrogen atmosphere. Catalyst components were introduced via common syringe techniques and polymerizations were conducted in a Parameter Generation & Control Inc. (PGC) constant temperature water bath equipped with an adjustable speed motorized tumbler. Polymerizations were terminated by treating the live polymer cement with an isopropanol/antioxidant solution. Polymer was recovered by pouring the polymer cement into pans and drying in vacuo at 60° C. Conversion data was determined gravimetrically.

Batch polymerizations were also conducted in a 6-liter reactor. The reactor was equipped with a variable speed agitator and a heating/cooling jacket to control the reactor temperature via a distributed Foxboro control system. A representative procedure for conducting a polymerization was to first fill the reactor with hexane and pickle with 10 mL of a 20 weight percent TIBA solution at 65° C. The pickled hexane was then dumped from the reactor and the reactor was blown down with dry nitrogen for five minutes. Approximately 1600 grams of 15 weight percent % isoprene premix, was charged into the reactor. After the reactor temperature reached the set point of 65° C., a pre-determined amount of preformed catalyst was charged into the reactor using a syringe via the injection port on the reactor. The reaction then commenced and samples of the reaction mixture were taken via a dipleg during the course of polymerization for residual monomer analysis utilizing gas chromatography (GC). The GC results were used to calculate monomer conversions with time, which were then used for a kinetic description of the propagation reaction.

Characterization.—Size-exclusion chromatography (SEC) was performed using a Wyatt Technologies miniDawn light scattering detector coupled with a Hewlett Packard 1047A refractive index detector. Polymer Laboratories B, C, and D mixed microgel columns were utilized with tetrahydrofuran as the carrier solvent at a flow rate of 0.35 ml/min and a column temperature of 40° C. Sample preparation involved filtering a 0.12 weight percent solution of polymer in THF through a 1.0 µm filter prior to injection. Polystyrene standards were used to calibrate the instrument.

Thermal field flow fractionation (ThFFF) was carried out on a FFFractionation LLC, Model T-100 Polymer Fractionator equipped with a Wyatt Dawn DSP laser photometer. THF was used as the carrier solvent at a flow rate of 0.2 ml/min. Samples were injected as unfiltered 0.12 weight percent solutions of polymer in THF.

Polymer microstructure was determined by C-13 solution NMR on a Varian Mercury VX-300. 10 wt % $CDCl_3$ solutions with 0.01 M $Cr(AcAc)_3$, and gated decoupling was employed. The methyl resonances at 23 ppm for cis (1,4), 18 ppm for (3,4), and 16 ppm for trans (1,4), were used to determine the microstructure.

Dilute solution viscosity (DSV) was measured using 0.2 wt % solutions of polyisoprene in toluene at 30° C. Cold flows were measured at 50° C. for 30 minutes.

Synthesis of Polyisoprene Rubber

Neodymium salts activated with aluminum alkyl co-catalysts have been known to catalyze the polymerization of conjugated dienes since the early 1960's. To date, many papers and patents have been published which describe variations and improvements to the original systems (see U.S. Pat. Nos. 3,297,667; 3,676,411; 3,794,604; L. Porri, G. Ricci, A. Giarrusso, N. Shubin, Z. Lu, in P. Arjunan, J. E. McGrath, T. L. Halon Eds., *ACS Symposium Series* 749, 15 (2000); F. Cabassi, S. Italia, G. Ricci, L. Porri, in R. P. Quirk Ed., *Transition Metal Catalyzed Polymerization*, Cambridge University Press, Cambridge UK, 1988, p. 655; and N. G. Marina, Y. B. Monakov, S. R. Rafikov, Kh. K. Gadeleva *Polym. Sci. USSR,* 26, 1251 (1984)). Much of this work was driven by the eventual commercialization of high cis-polybutadiene in the 1980s for the use in tire applications (see U.S.

Pat. Nos. 4,242,232; 4,260,707; 4,699,960; and 4,444,903). Although isoprene is also easily polymerized by neodymium it has remained mostly of academic interest as a model for lanthamide type polymerizations due to it ease of handling (boiling point of 34° C. versus −4.5° C. for butadiene). In either case, the type of catalyst system employed, and its method of preparation, is crucial to the success of the polymerization.

Traditionally, there are two main types of catalyst systems (see L. Porri, A. Giarrusso, in G. C. Eastmond, A. Ledwith, S. Russo, P. Sigwalt Eds., *Comprehensive Polymer Science* Part II, Vol. 4, Pergamon Press, Oxford, 1989, page 53), the first is a ternary system based on soluble neodymium carboxylates in conjunction with an alkylaluminum co-catalyst and a halogen source (see R. P. Quirk, A. M. Kells, K. Yunlu, J. P. Cuif, Polymer 41, 5903 (2000); and A. Pross, P. Marquardt, K. H. Reichert, W. Nentwig, T. Knauf, *Angew. Makromol. Chem.* 211, 89 (1993)). The second system is a binary catalyst comprising of an insoluble neodymium halide complexed with three equivalence of a Lewis base such as an alcohol, amine, or phosphonate and an alkylaluminum activator (see H. Iovu, G. Hubca, E. Simionescu, E. Badea, J. S. Hurst, *Eur. Polymer J.* 33, 811 (1997); H. Iovu, G. Hubca, D. Racoti, J. S. Hurst, *Eur. Polymer J.* 35, 335 (1999); J. H. Yang, M. Tsutsui, Z. Chen, D. Bergbreiter, *Macromolecules* 15, 230 (1982)). In general, the two systems behave similarly; however, the homogeneous ternary system appears to have gained acceptance commercially in the production of polybutadiene (see D. J. Wilson, *J. Polym. Sci., Part A*. 33, 2505 (1995)). As with other cis specific transition metal based systems, a halogen must be present for neodymium to catalyze high cis-polymerizations (see H. L. Hsieh, H. C. Yeh, *Rubber Chem. Techno.*, 58, 117 (1985)). Chloride and bromide derivatives make the most active catalysts but the cis content is equally high for fluoride or iodide complexes as well. Typically, the most active systems consist of treating a branched long chain neodymium carboxylate with branched trialkyl-aluminum or dialkylaluminum hydrides, in an Al/Nd ratio between 10-40/1, and the use of 2-3 equivalents of a halide source, such as diethylaluminum chloride or tert-butylchloride (see D. J. Wilson, Polymer 34, 3504 (1993)). Polymer molecular weight is inversely proportional to overall catalyst levels as well as aluminum alkyl concentration (see J. B. Nickaf, R. P. Burford, R. P. Chaplin, *J. Polym. Sci., Part A*. 33, 1125 (1995)).

Equally important as the type of reagents used is the method by which the active catalyst is prepared. The simplest method is to generate the catalyst in-situ by sequentially introducing the catalyst components to the polymerization solution. It is usually most effective to introduce the aluminum alkyl components first, thereby scavenging impurities from the premix prior to contact with the neodymium salt. The other method for catalyst preparation is to preform the catalyst before it is introduced into the polymerization vessel. The most common practice involves preforming in the presence of at least a few equivalents of monomer (see L. Porri, G. Ricci, A. Giarrusso, N. Shubin, Z. Lu, in P. Arjunan, J. E. McGrath, T. L. Halon Eds., *ACS Symposium Series* 749, 15 (2000); F. Cabassi, S. Italia, G. Ricci, L. Porri, in R. P. Quirk Ed., *Transition Metal Catalyzed Polymerization*, Cambridge University Press, Cambridge UK, 1988, p. 655; and N. G. Marina, Y. B. Monakov, S. R. Rafikov, Kh. K. Gadeleva *Polym. Sci. USSR*, 26, 1251 (1984)). In this fashion a stable Nd-allyl is generated in favor of a thermally unstable Nd-alkyl leading to a more active catalyst solution.

Although many variations of the basic principle of catalyst preparation and polymerization exist for a batch process, very little has been disclosed on how certain parameters affect the continuous polymerization of polyisoprene. We therefore, set about defining a neodymium system amenable to the large scale continuous polymerization of isoprene.

In-Situ Catalyst Make-Up.—Initially we focused on in-situ catalyst generation utilizing the homogenous ternary system. Small scale batch polymerizations were conducted in glass bottles charged with 18 wt % isoprene/hexane premix with the ultimate goal of determining the molecular weight dependence on the type of aluminum alkyl co-catalyst used. Catalyst components were charged sequentially via syringes in the order of aluminum alkyl, neodymium versatate, then dialkylaluminum chloride. The dependence of molecular weight on triisobutylaluminum (TIBA) versus diisobutyl-aluminum hydride (DIBAL) at various catalyst levels and aluminum-alkyl ratios is shown in Table 1. At high catalyst levels, 0.25 millimoles of neodymium per hundred grams of isoprene monomer (mmphm) and high levels of aluminum-alkyl, 30 molar equivalents to neodymium, in-situ catalyst generation was very efficient regardless of aluminum-alkyl type. For example, two hour conversion reached 90% or better for both DIBAL and TIBA (entry 1 and 2). However, the molecular weight and molecular weight distribution (MWD) of the two materials were significantly different. Switching from TIBA to DIBAL resulted in a 50% reduction of the Mw and a significant increase in MWD.

TABLE 1

Comparison of TIBA and DIBAL-H in an in-situ Catalyst System

| Entry | Nd level (mmphm) | TIBA (eq) | DIBAl-H (eq) | Conversion (%) | Mn (×1000) | Mw (×1000) | Mw/Mn (MWD) |
|---|---|---|---|---|---|---|---|
| 1 | 0.25 | 30 | — | 89 | 309 | 821 | 2.66 |
| 2 | 0.25 | — | 30 | 94 | 98 | 391 | 3.96 |
| 3 | 0.25 | 15 | — | 55 | 805 | 1444 | 1.79 |
| 4 | 0.25 | — | 15 | 90 | 265 | 707 | 2.66 |
| 5 | 0.15 | 30 | — | 64 | 484 | 1095 | 2.26 |
| 6 | 0.15 | — | 30 | 70 | 187 | 588 | 3.14 |
| 7 | 0.15 | 15 | — | 18 | 929 | 1617 | 1.74 |
| 8 | 0.15 | — | 15 | 54 | 485 | 1079 | 2.22 |

Conditions: 100 mL of 18 wt % isoprene in hexane polymerized in bottles at 65° C. for 2 hours Lowering the catalyst level to 0.15 mmphm Nd, but maintaining a ratio of 30 eq. of aluminum-alkyl (entry 5 and 6), resulted in a drop in two hour conversion to 65-70% for both systems, a narrowing of MWD and an increase in molecular weight. Again, there was a 50% reduction in molecular weight when DIBAL was used in place of TIBA. Further increases in molecular weight were possible by lowering the ratio of Al to Nd from 30:1 down to 15:1. Although significantly higher molecular weights were achieved, there was a sharp decline in rate of polymerization for the TIBA system. At 0.25 mmphm Nd conversion dropped from 90% in 2 hours with 30 eq. of TIBA (entry 1) to just 55% when 15 eq. of TIBA was employed (entry 3). Conversion in the DIBAL system however was only slightly affected by the drop in aluminum level (entry 2 and 4). These results clearly demonstrate the superior alkylating ability of DIBAL which leads to the formation of more active species and therefore higher conversion than in the TIBA system. The molecular weight data is also consistent with aluminum-hydride species being much more effective chain transfer agents then aluminum-alkyls leading to broader, as well as lower, molecular weight materials. It is interesting to note that similar conversion, molecular weight, and molecular weight distribution was achieved with 0.15 mmphm Nd utilizing either 15 eq. of DIBAL or 30 eq. of TIBA (entry 5 and 8).

In order to assess the feasibility of these systems for the production of a commercial Nd-PI, a Mooney versus molecular weight correlation for the TIBA system was generated (Table 2). Two different catalyst levels, 0.15 and 0.25 mmphm Nd, and three different aluminum alkyl ratios, 15, 25, and 35 eq., were employed. As expected, increasing aluminum levels significantly decreased molecular weight, and therefore Mooney viscosity (entry 1 and 3).

TABLE 2

Mooney versus Molecular Weight at Different TIBA and Nd Levels

| Entry | Nd level (mmphm) | TIBA (eq) | Conversion (%) | $ML_{1+4}$ (100° C.) | Mn (×1000) | Mw (×1000) | Mw/Mn (MWD) |
|---|---|---|---|---|---|---|---|
| 1 | 0.15 | 15 | 63 | 68 | 763 | 1479 | 1.93 |
| 2 | 0.15 | 25 | 83 | 53 | 618 | 1297 | 2.10 |
| 3 | 0.15 | 35 | 94 | 34 | 401 | 965 | 2.40 |
| 4 | 0.25 | 15 | 80 | 61 | 751 | 1393 | 1.86 |
| 5 | 0.25 | 25 | 96 | 34 | 396 | 905 | 2.28 |
| 6 | 0.25 | 35 | 99 | 19 | 201 | 656 | 3.26 |

Figure 24:
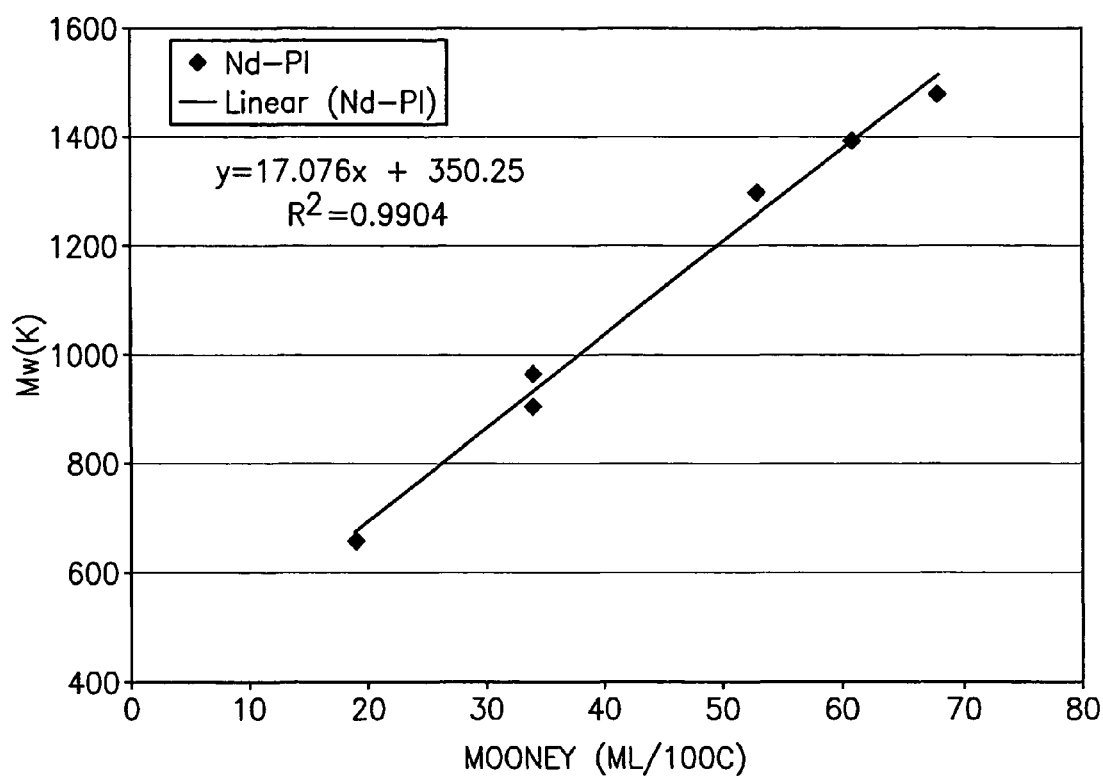
FIG. 24 is a graph showing the linear correlation between Mooney viscosity and molecular weight.

Conditions: 500 mL of 15 wt % isoprene in hexane polymerized in bottles at 65° C. for 6 hours A plot of the data presented in Table 2 suggests a linear correlation ($r^2$=0.990) of Mooney viscosity on molecular weight in the neodymium system under study (FIG. 24). Mooney viscosity has long been used as a predictive tool for polymer processability in the rubber industry (see F. J. Male, *Rubber World* August, 73 (1994)). Currently, titanium catalyzed high cis-polyisoprene is commercially available in two different Mooney ranges, a high Mooney material centered around 80 and a low Mooney material centered near 60. Likewise, high and low Mooney versions of Li-PI are also commercially available. Therefore, the in-situ TIBA system employed in this study is only on the edge of viability in terms of production of high Mooney material.

Figure 25:
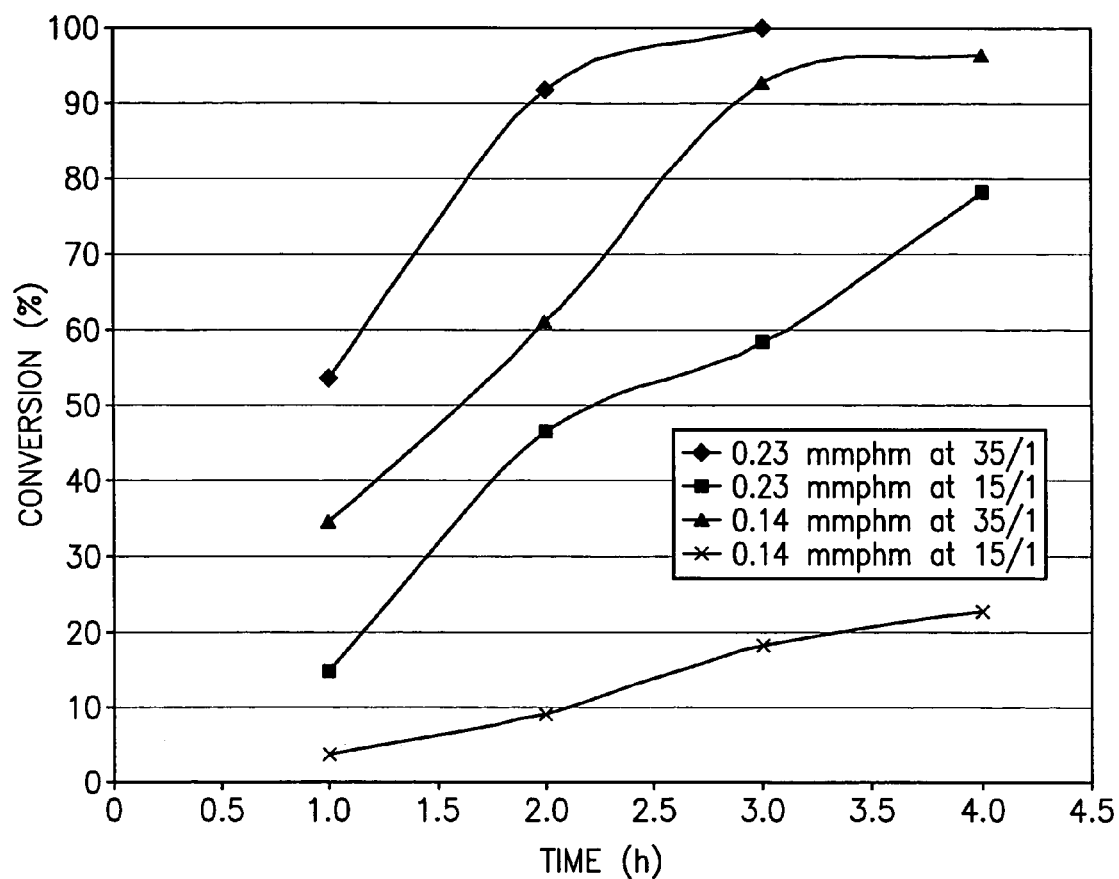
FIG. 25 is a graph showing conversion versus time at various neodymium levels and TIBA ratios.

Although the Mooney could be driven higher by using less catalyst or less aluminum, the trade-off in conversion would be severe. For example, a plot of isoprene conversion versus time for the in-situ catalyst system TIBA/Nd/DIBAl-Cl at various ratios of TIBA, and at both a high and low level of Nd, is shown in FIG. 25.

Reasonable rates of polymerization were achieved at either level of Nd so long as 35 eq. of TIBA was used. However, it is predicted using the relationship in FIG. 1, that these systems will produce only 25 to 35 Mooney material. Dropping the aluminum ratio to 15 eq. in an attempt to raise molecular weight, significantly slowed down the rate of polymerization. At 0.23 mmphm Nd three hour conversion moved from 95% when 35 eq. of TIBA was used to 60% when 15 eq. of was utilized. This relationship was even more dramatic at a level of 0.14 mmphm Nd. The use of 35 eq. TIBA gave 95% conversion in three hours but 15 eq. TIBA gave a conversion of just 20% at this low catalyst level. It is therefore unlikely that an in-situ system based on the classic ternary system will be useful for the production of high Mooney polyisoprene with a reasonable rate of conversion. It should be noted that this limitation is not a factor in the polymerization of butadiene which can achieve full conversion in under one hour.

Nevertheless, the effectiveness of polymerizing isoprene fed continuously with an in-situ catalyst system was explored using a three reactor chain equipped with a 3.8-liter and two 7.6-liter stirred tank reactors. Premix was continuously fed into the first reactor while polymer cement was continuously collected out of the third reactor into a hold tank. Residence times were established at one hour in the first reactor and two hours in each of the remaining two reactors allowing for a total reaction time of five hours and a total run time of nearly 90 hours. An in-situ catalyst make-up system was used that first introduced a flow of TIBA to Nd(versatate)$_3$ down stream of an in-line dynamic mixer. After the mixer, a flow of DIBAl-Cl was introduced in-line and this three component mixture was fed into the first reactor. Regardless of conditions and make-up parameters the best conversions achieved from an in-situ system was at 0.3 mmphm Nd with 35 eq. of TIBA. Even at these higher levels, conversions reached just 23% in the first reactor, 46% in the second, and 55% conversion in the third reactor. Molecular weight was very broad with an Mn of 77,000 and an Mw of 323,000 for a MWD of 4.2. Apparently, catalyst formation was sluggish, and initiation was occurring throughout the first and second reactors. Clearly, conversion from this in-situ process is too low for commercial production of Nd-PI.

Figure 26:
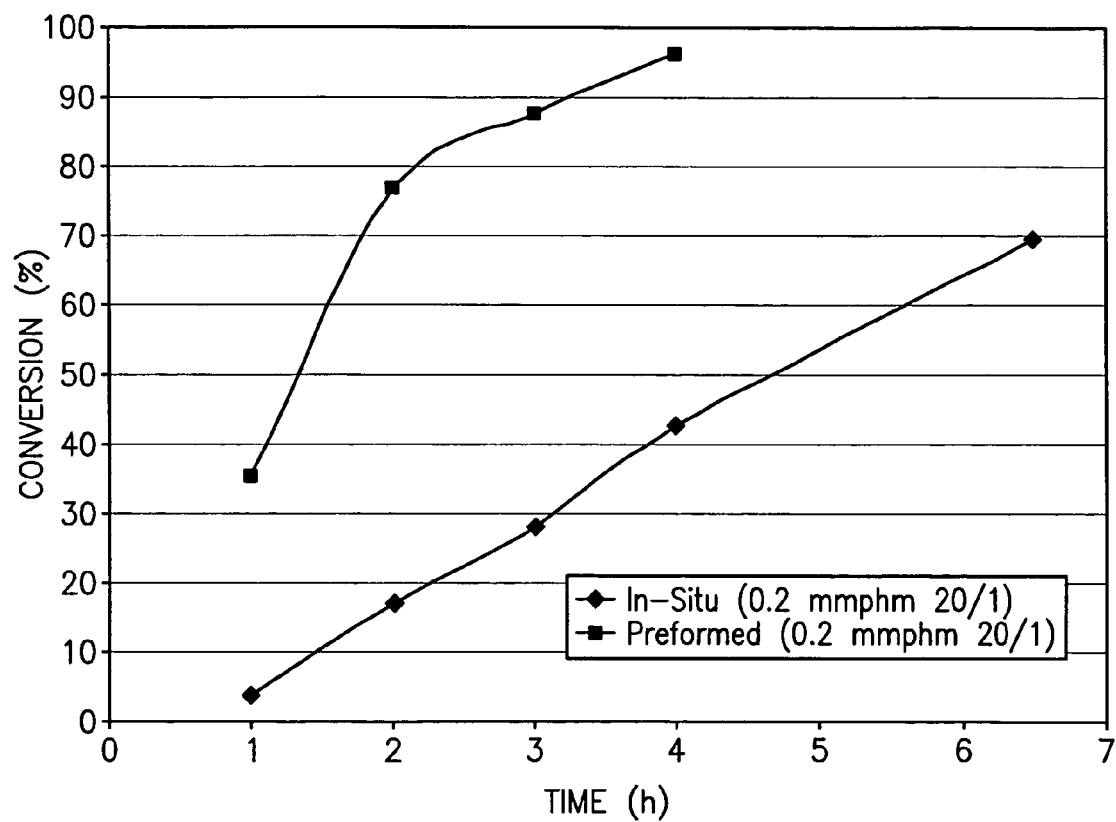
FIG. 26 is a graph showing the relationship between conversion and polymerization time.

Preformed Catalyst Make-Up.—The most convenient approach to increasing the activity of the ternary neodymium system is by preforming the catalyst components prior to their introduction into the polymerization reactor. This can be accomplished by treating a small quantity of isoprene sequentially with aluminum alkyl, neodymium soap, and dialkylaluminum chloride followed by an aging period at 65° C. The resulting golden colored solutions can be stored under nitrogen for days and can be used directly as a single component catalyst solution. A comparison of conversion versus time for an in-situ system comprised of TIBA/Nd/DIBAlCl (in a ratio of 20/1/2.5 charged at 0.2 mmphm Nd) with a preformed system of the exact same ratios (aged in the presence of 15 eq. of isoprene for 90 minutes at 65° C.) is shown in FIG. 26. It is quite clear that the rate of conversion, determined gravemetrically in this bottle study, was significantly faster for the preformed system. Conversion at 4 hours is about 45% for the in-situ catalyst while the preformed catalyst gave over 95% conversion in the same amount of time.

Figure 27:
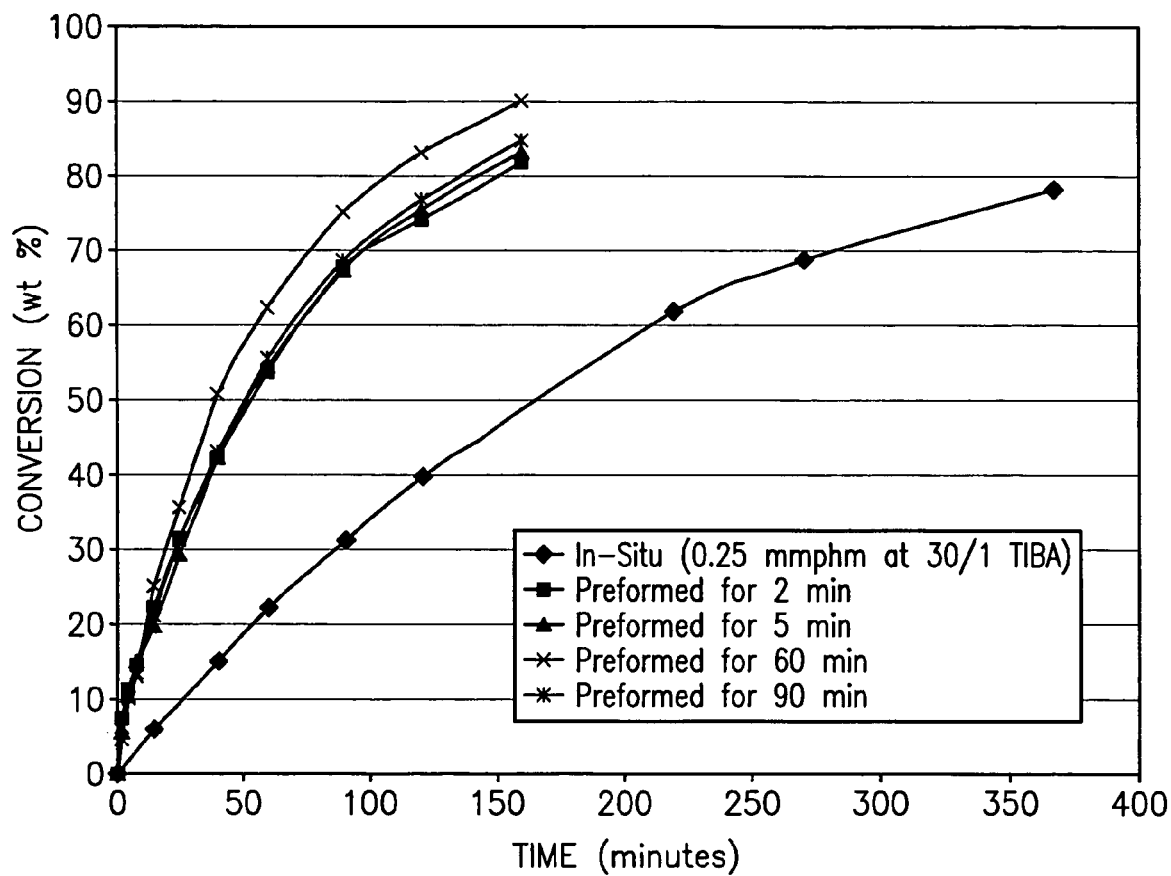
FIG. 27 is a graph showing dependence of activity on aging time in a preformed catalyst.

A kinetic study exploring the dependence of preformed catalyst activity on aging time at 65° C. was undertaken in a 6-liter stirred tank reactor. Conversion versus time curves were generated at 0.25 mmphm Nd preformed with TIBA/Nd/DIBAlCl in a ratio of 30/1/2.5 in the presence of 50 equivalents of isoprene. Conversion was determined by GC analysis of residual isoprene remaining in aliquots of polymer cement withdrawn from the reactor in sealed vials at appropriate time intervals. As shown in FIG. 27, GC analysis confirmed that preforming the catalyst resulted in an increase in polymerization rate. There was also very little dependence on the amount of time needed for the catalyst to reach optimal activity under these specific conditions. Surprisingly, a catalyst preformed at 65° C. for two minutes was as active as one preformed for 90 minutes. Presumably there would be a greater dependence on activity with time in the case of low temperature aging (see F. J. Male, *Rubber World* August, 73 (1994)).

Figure 28:
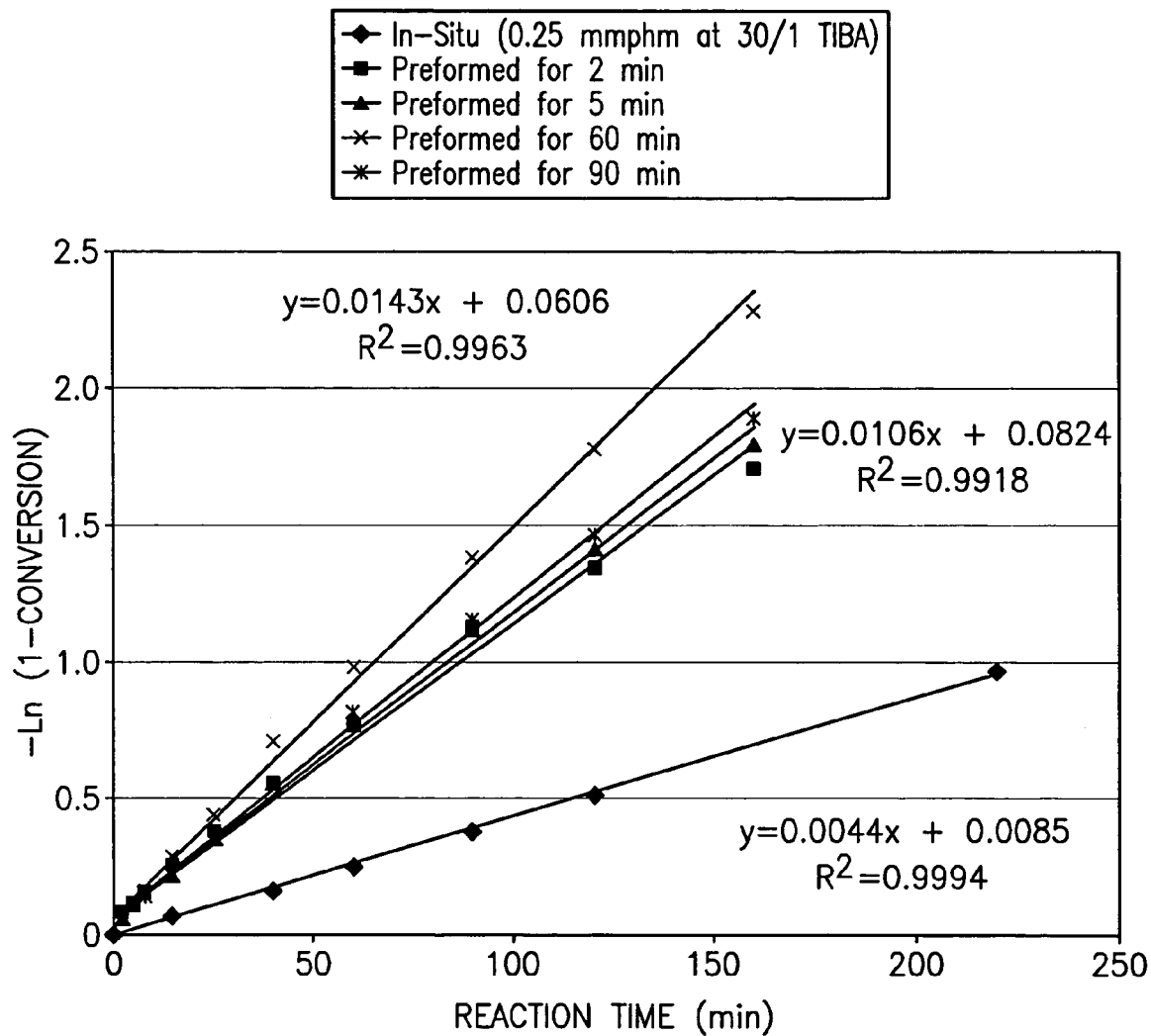
FIG. 28 is a graph showing Ln (1-conversion) versus reaction time.

Re-plotting FIG. 27 as a first order rate plot with respect to monomer concentration shows a linear dependence of conversion on time (FIG. 28). The slope of these lines represents the rate constant for polymerization under the conditions described.

Figure 29:
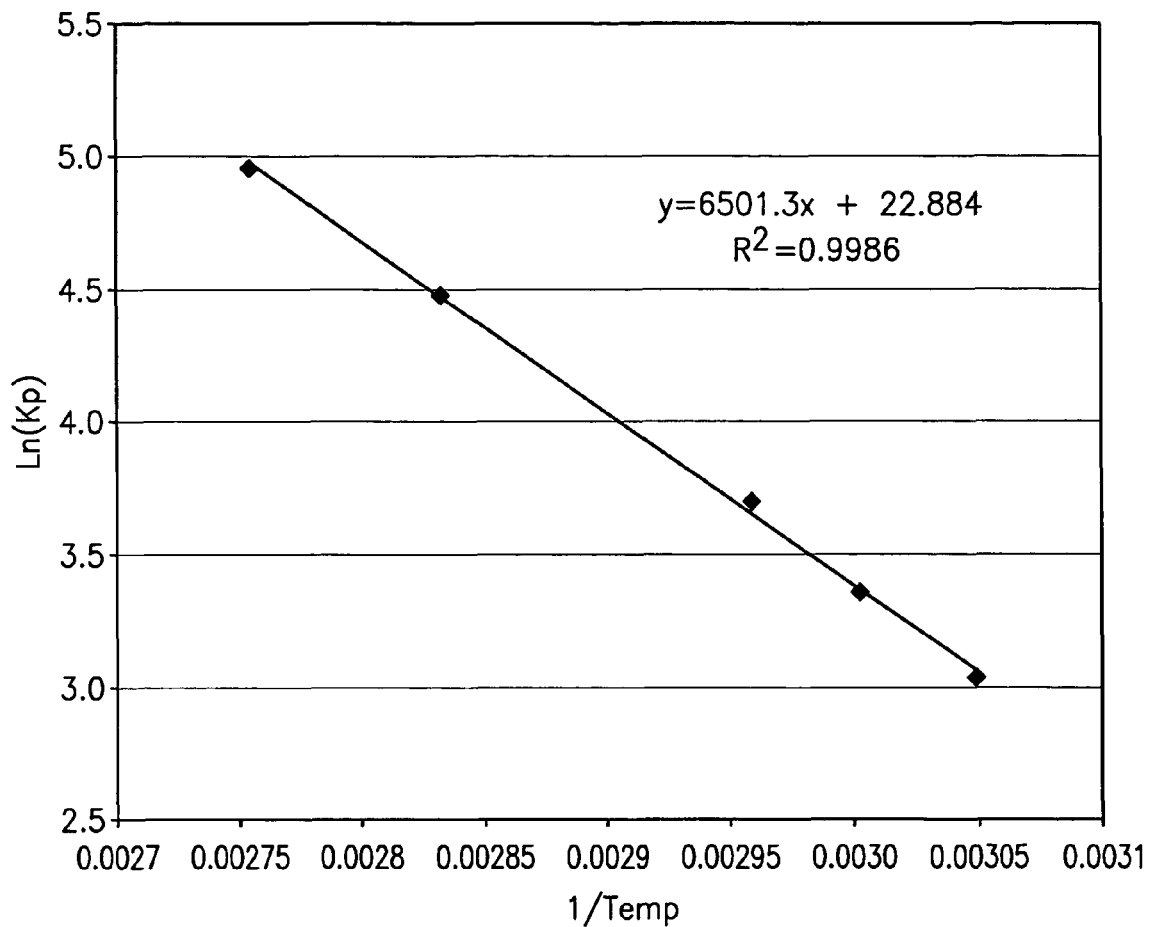
FIG. 29 is a graph showing isoprene homopolymerization activation energy.

The average rate of polymerization (kp) for the four different preformed systems was 0.0125 min$^{-1}$, where as the kp for the in-situ catalyst was 0.0042 min$^{-1}$. This change in rate represents a three fold increase in the rate of polymerization for the preformed catalysts. It is suspected that the increase in rate is not due to a lowering of the activation energy of polymerization but to an increase in the number of active sites initially available for polymerization. Therefore, the rate of polymerization in this system is more accurately described as Kp=kpC, where C is the concentration of active sites. The apparent activation energy for preformed neodymium isoprene polymerization was determined by creating an Arrhenius plot (FIG. 29). Plotting the natural log of kp determined at six different temperatures versus 1/T gave a linear relationship corresponding to an activation energy of 12.9 kcal/mol. The activation energy for isoprene polymerization using an in-situ neodymium catalyst has previously been determined to be just 8.2 kcal/mol (see H. L. Hsieh, H. C. Yeh, Rubber Chem. Techno, 58, 117 (1985)).

With a three fold increase in the rate of polymerization for preformed catalysts, it was anticipated that higher Mooney material could now be formed at a reasonable rate even at low levels of catalyst and aluminum alkyl. A comparison of molecular weight dependence on DIBAL versus TIBA was again conducted, but this time utilizing the preformed catalyst make-up technique (Table 3). Polymerizations were conducted by first generating four different preformed catalysts. Two were comprised of TIBA, using 10 and 20 eq. to neodymium, and two were prepared with 10 and 20 eq. of DIBAL. Each contained 15 eq. of isoprene and 2.5 eq. DIBAlCl and were aged at 65° C. for one hour.

TABLE 3

Comparison of TIBA and DIBAL in Preformed Catalysts

| Entry | TIBA (eq) | DIBAL-H (eq) | Conversion (%) | Mn (×1000) | Mw (×1000) | Mw/Mn (MWD) |
|---|---|---|---|---|---|---|
| 1 | 10 | — | 9.3 | — | — | — |
| 2 | 20 | — | 73 | 1780 | 3260 | 1.84 |
| 3 | — | 10 | 64 | 1570 | 2730 | 1.70 |
| 4 | — | 20 | 87 | 386 | 1620 | 4.20 |

Conditions: 100 mL of 18 wt % isoprene in hexane polymerized at 0.2 mmphm Nd and 65° C. for 3 hours It was obvious that preforming with just 10 eq. of TIBA resulted in a non-active catalyst at 0.2 mmphm Nd (entry 1). However, the use 10 eq. of DIBAL yielded a viable catalyst capable of yielding 64% conversion in three hours (entry 3). This was only slightly less active than when 20 eq. of TIBA was used (entry 2). The most active catalyst was produced from 20 eq. of DIBAL giving 90% conversion in three hours (entry 4). This catalyst however produced a polymer with a very broad molecular weight distribution with an Mn of just 380,000. It is expected that this material would have excellent processing characteristics but lack certain desirable mechanical properties due to the high MWD. As was noted earlier in Table 1, under the right in-situ conditions, DIBAL and TIBA could be used at appropriate levels to generate almost the identical polymer. This was again the case for preformed catalysts. For example, the 20 eq. TIBA catalyst produced a polymer with an Mn of 1.78 million and a MWD of 1.8 (entry 2) while the 10 eq. DIBAL catalyst gave a material with an Mn of 1.57 million and a MWD of 1.7 (entry 3). Both of these systems were reasonably active and possessed the ability to produce high molecular weight material. For this reason, each were examined separately at different neodymium levels in order to establish a Mooney vs. catalyst level correlation (Table 4). Polymerizations were initiated by both catalyst systems at three different levels, 0.15, 0.20, and 0.25 mmphm Nd. Four hour conversions were all over 90%.

TABLE 4

Mooney versus Preformed Neodymium Levels and Type

| Entry | Al-Alkyl (type) | Nd level (mmphm) | $ML_{1+4}$ (100° C.) | Mn (×1000) | Mw (×1000) | Mw/Mn (MWD) |
|---|---|---|---|---|---|---|
| 1 | DLBAl-H | 0.15 | 80.2 | 1109 | 2050 | 1.85 |
| 2 | DIBAl-H | 0.20 | 68.8 | 792 | 1675 | 2.12 |
| 3 | DIBAl-H | 0.25 | 55.7 | 663 | 1613 | 2.43 |
| 4 | TIBA | 0.15 | 85.7 | 1190 | 2347 | 1.97 |
| 5 | TIBA | 0.20 | 75.0 | 939 | 1992 | 2.12 |
| 6 | TIBA | 0.25 | 70.0 | 786 | 1679 | 2.14 |

Conditions: 500 mL of 16 wt % isoprene in hexane polymerized in bottles at 65° C. for 4 hours In the case of the 10 eq. DIBAL catalyst, Mooney ranged from 80.2 at 0.15 mmphm Nd (entry 1) to 55.7 at 0.25 mmphm Nd (entry 3) representing a range of 25 Mooney points. Mw for these materials ranged from 2.0 million with a MWD of 1.85 down to 1.6 million and a MWD of 2.43. The 20 eq. TIBA catalyst produced a polymer with a Mooney of 85.7 at 0.15 mmphm Nd (entry 4) and 70.0 Mooney at 0.25 mmphm Nd (entry 6) which is just a 15 point Mooney drop over the same catalyst range as the DIBAL system. It is of significant practical importance to observe the broadening of molecular weight distribution as well as the increase in the spread of Mooney between 0.15 mmphm Nd and 0.25 mmphm Nd for DIBAL versus TIBA. It was expected that a continuous polymerization process would lead to broader MWD and lower Mooney than that predicted by batch polymers at the same catalyst level. It is therefore likely that continuous TIBA systems will behave more closely to their batch counterparts allowing for the production of materials with high Mooney and relatively narrow molecular weight distributions compared to the DIBAL system.

A second experiment focusing only on the TIBA system was run using three preformed catalyst varying in the amount of TIBA from 20, 25, and 30 equivalents (Table 5). Each catalyst was used at levels of 0.15, 0.20, and 0.25 mmphm Nd resulting in 9 different polymerizations.

TABLE 5

Mooney Comparison at Different Levels and TIBA Ratios for Nd Preform

| Entry | TIBA (eq) | Nd level (mmphm) | Conversion (%) | $ML_{1+4}$ (100° C.) | Mn (×1000) | Mw (×1000) | Mw/Mn (MWD) |
|---|---|---|---|---|---|---|---|
| 1 | 20 | 0.15 | 64.8 | 82.9 | 1215 | 2034 | 1.7 |
| 2 | 20 | 0.20 | 89.8 | 74.8 | 859  | 1572 | 1.8 |
| 3 | 20 | 0.25 | 94.8 | 71.6 | 830  | 1563 | 1.9 |
| 4 | 25 | 0.15 | 79.6 | 74.0 | 934  | 1663 | 1.8 |
| 5 | 25 | 0.20 | 94.0 | 65.1 | 737  | 1449 | 2.0 |
| 6 | 25 | 0.25 | 98.4 | 59.7 | 613  | 1324 | 2.1 |
| 7 | 30 | 0.15 | 87.4 | 61.0 | 680  | 1367 | 2.0 |
| 8 | 30 | 0.20 | 97.0 | 51.5 | 498  | 1181 | 2.4 |
| 9 | 30 | 0.25 | 98.4 | 39.4 | 358  | 971  | 2.7 |

Figure 30:
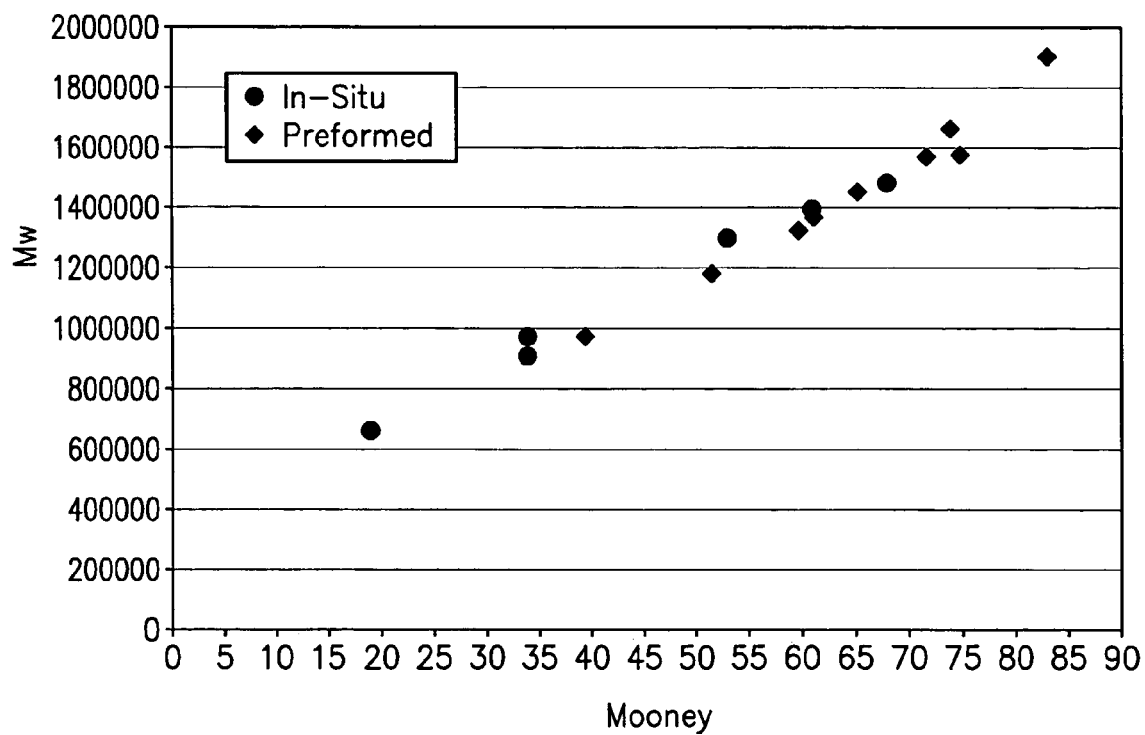
FIG. 30 is a graph of Mooney viscosity versus molecular weight for in situ and preformed catalysts.

Conditions: 500 mL of 15 wt % isoprene in hexane polymerized in bottles at 65° C. for 4 hours As expected from Table 4, the preformed catalyst with 20 eq. of TIBA gave a Mooney of 83 at 0.15 mmphm Nd and 71.6 at 0.25 mmphm Nd (entry 1-3). Preformed catalyst with 25 eq. TIBA gave a 10 point lower Mooney of 74 at 0.15 mmphm Nd and a Mooney of 59.7 at 0.25 mmphm Nd (entry 4-6). Finally, the preformed catalyst made with 30 eq. of TIBA gave a 61 Mooney polymer at 0.15 mmphm Nd and just 39.4 Mooney material at 0.25 mmphm Nd. The data suggests that a more significant change in Mooney is achieved when extra aluminum alkyl is used in the preformed catalyst than when overall neodymium levels are increased. For example, moving from 0.15 mmphm Nd with 20 eq. TIBA (or 3.0 mmphm Al) to 0.15 mmphm Nd with 30 eq. TIBA (4.5 mmphm Al) resulted in a Mooney change from 82.9 to 61.0, a 22 point Mooney drop. Moving from 0.15 mmphm Nd with 20 eq. TIBA (3.0 mmphm Al) to 0.25 mmphm Nd with 20 eq. (5.0 mmphm Al), an overall larger increase in aluminum concentration, drops of Mooney just 12 points. Combining these factors, catalyst level with aluminum ratio, allows for a predictive method of obtaining a desired Mooney. Superimposing a plot of Mooney vs. MW from Table 4, with that of the already shown linear correlation from Table 2 for in-situ catalysts, shows an extension of this relationship to preformed catalysts (FIG. 30). It is clear that production of higher Mooney material is consistently achieved through the use of preformed catalysts.

To test the ability of preformed neodymium catalysts to polymerize isoprene continuously, the same three reactor chain described above was used. A batch of 20 eq. TIBA preformed catalyst was first prepared in an isolated 3.8-liter reactor. The homogenous catalyst was then continuously fed into the first reactor of the three reactor chain. Premix and catalyst flow rates were adjusted to achieve a level of 0.25 mmphm Nd. Conversion in the first reactor lined out at 50%, the second reactor 80% and the third reactor near 95%. Isolated polymer samples showed the Mooney ranging between 70.6 to 74.6 over a 20 hour run period. This correlates very well with results obtained from batch polymerizations (Table 5, entry 3). Lowering catalyst flow rates to achieve a catalyst level of 0.15 mmphm Nd had the anticipated effects of lowering conversions and raising the molecular weight. Under these conditions, the first, second, and third reactor conversions decreased to 20, 60, and 85% respectively. Mooney's of isolated material during this period rose to 80 with an average molecular weight of 1.5 million and MWD of 2.1. A second preformed catalyst was used to achieve 50 and 60 Mooney material by using 30 equivalents of TIBA during the catalyst make-up. As previously noted a good correlation with predicted Mooney from batch trials was observed. These results demonstrate the versatility and effectiveness of preformed neodymium catalysts for the continuous polymerization of isoprene.

Polymer Characterization

Polymer microstructure.—One of the characteristics of neodymium catalysts is their ability to polymerize both butadiene and isoprene with a high 1,4-cis microstructure. In the systems under study, the 80 Mooney material prepared from a 20 eq. TIBA preformed catalyst had a microstructure, determined by $^{13}C$ NMR, of 96.6% cis, 0.2% trans, and 3.2% 3,4. This microstructure remained nearly unchanged when a 30 eq. TIBA preformed catalyst was used to generate a 64 Mooney polymer (97.0% cis, <0.1% trans, 3.0% 3,4). The lack of sensitivity of microstructure on catalyst composition is also evident by the fact that both materials had the same glass transition temperatures. The higher Mooney sample had a Tg of –64.4° C. while the low Mooney polymer had a Tg of –64.6° C. It has been noted previously that changes in aluminum ratio have only a minor effect on polyisoprene microstructure. An interesting feature of Nd-PI is the lack of an appreciable trans content. This is in contrast to that of titanium catalyzed polyisoprene. Typically, Ti-PI has a cis content of 98% with the remainder of the polymer being made up of 1.5% trans and 0.5% 3,4. This gives the material an overall 1,4-content of 99.5% versus just 97% for the neodymium polymers. The higher total-1,4-content is responsible for Ti-PI having a lower Tg of –67.0° C. As has been stated earlier, Li-PI has a cis content closer to 90% with the remainder being 6-7% trans and 3-4% 3,4. With a total 1,4-content close to that of Nd-PI, these two materials have very similar glass transition temperatures (Li-PI Tg=–64.3).

Polymer Macrostructure.—Polymer macrostructure as a measure of molecular weight, molecular weight distribution, branching and gel fraction, varies greatly between Nd-PI and conventional Ti-PI. This is clearly seen when a comparison of molecular weight at similar Mooney is made between the two types of materials (Table 6). For an 80 Mooney Ti-PI, size exclusion chromatography (SEC) measured an Mn of 495K, Mw of 1.2 million and MWD of 2.5. Nd-PI with the same Mooney however, had twice the Mn of 1.1 million, a Mw of over 1.8 million and an MWD of 1.7. The discrepancy between Mooney and Mw for these two types of polyisoprene is made clear when the materials are subjected to thermal field flow fractionation (ThFFF) determination of molecular weight.

TABLE 6

Molecular Weight Data for Three Different Types of Synthetic Polyisoprene

|  |  | Ti-PI | Nd-PI | Li-PI |
|---|---|---|---|---|
| Mooney | $ML_{1+4}$ (100° C.) | 80 | 83 | 48 |
| $T_{80}$ | 2 minute decay | 0.76 | 0.49 | 1.1 |
| DSV | 30° C. | 2.97 | 4.04 | 4.02 |
| SEC | Mn | 495,000 | 1,080,000 | 756,000 |
|  | Mw | 1,230,000 | 1,810,000 | 2,115,000 |
|  | Mw/Mn | 2.5 | 1.7 | 2.8 |
|  | Mz | 2,500,000 | 4,100,000 | 3,400,000 |
| ThFFF | Mn | 810,000 | 1,400,000 | 1,000,000 |
|  | Mw | 2,490,000 | 2,800,000 | 2,500,000 |
|  | Mw/Mn | 3.1 | 2.0 | 2.5 |
|  | Mz | 25,900,000 | 4,165,000 | 3,965,000 |

Figure 31:
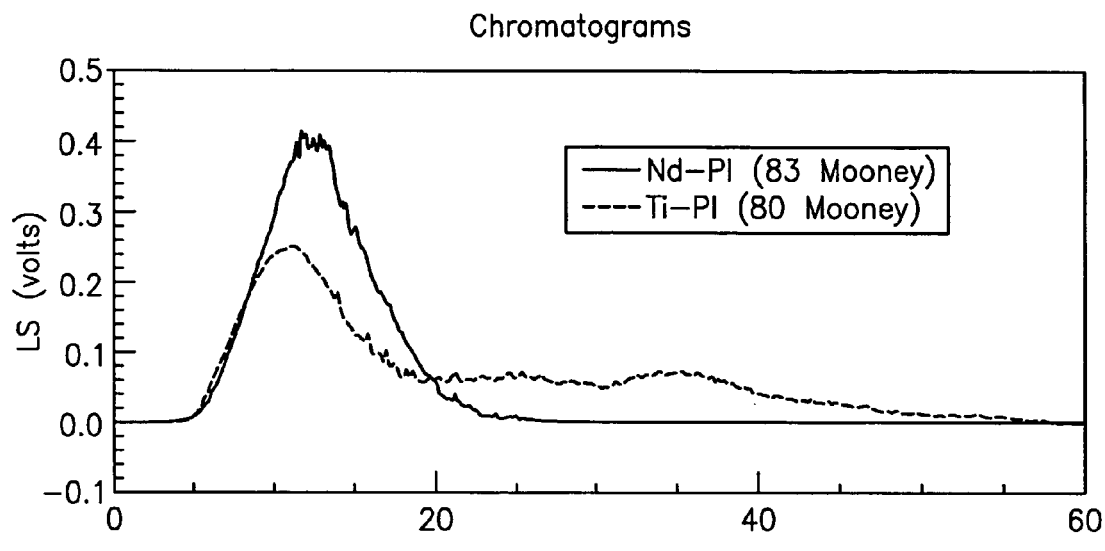
FIG. 31 is a graph of light scattering response versus time for neodymium-polyisoprene and titanium-polyisoprene.
Figure 32:
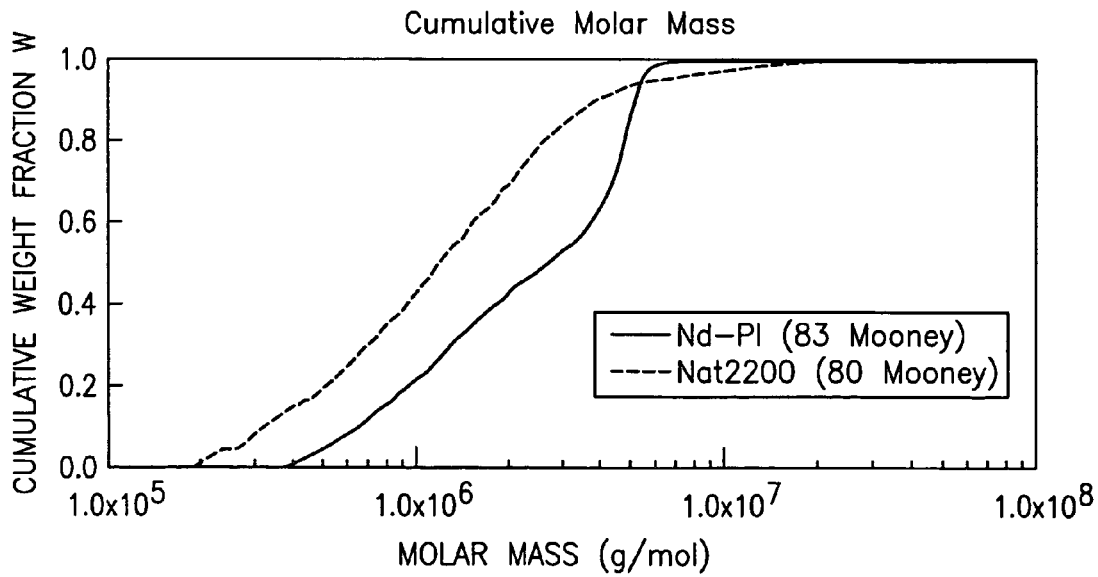
FIG. 32 is a graph of cumulative weight fraction versus molar mass for neodymium-polyisoprene and titanium-polyisoprene.

Unlike SEC, ThFFF does not require pre-filtering of the samples and there is no absorption of polymer on column packing materials. The use of a thermal field to separate molecular weight thus allows for nearly 100% mass recovery 1-5 and determination of molecular weights from 1000 to as high as 100 million. Comparing the Mw of Nd-PI with that of Ti-PI as determined through ThFFF, shows that Ti-PI actually has an unfiltered Mw of 2.5 million with a MWD of 3.1. Nd-PI is determined to have an Mw of 2.8 million. At such high molecular weights it is also important to examine Mz which is most sensitive to the high molecular weight fraction. For Nd-PI, SEC and ThFFF results both showed an Mz of 4.1 million. Ti-PI however had an SEC Mz of 2.5 million but on the ThFFF it was determined to be closer to 26 million! This difference in a high molecular weight fraction can be visually observed by comparing the ThFFF light scattering response between Ti-PI and Nd-PI (FIG. 31). It is clear that the Ti-PI contains an ultra high molecular weight fraction that elutes from the thermal field between 20 and 40 minutes. Nd-PI is completely recovered after 25 minutes. A plot of cumulative weight fraction versus molar mass shows that while nearly 100% of Nd-PI lies below 5 million, as much as 5% of Ti-PI lies above this molecular weight (FIG. 31).

A comparison of Nd-PI to Li-PI shows that these two materials have very similar high molecular weight profiles but the lithium material has a lower molecular weight tail. In fact, SEC analysis of Li-PI showed the material to be bimodal. This explains why Li-PI has a Mooney of just 48. It is interesting that the Li-PI with such a low Mooney does not display any cold flow behavior. Yet, 50 Mooney Nd-PI had a cold flow of 0.43 mg/min at 50° C. This appears to be related to the lack of entanglements or branching in the Nd-PI. The amount of entanglements can be measured through the use of stress relaxation data ($T_{80}$) in which long chain branching or chain entanglements increase a material's relaxation time (see C. B. Friedersdorf, Rubber World, January, 30 (1995)). The 50 Mooney Nd-PI had a $T_{80}$ of just 0.1 where as the Li-PI was very slow to relax yielding a T80 of 1.12. Such a large $T_{80}$ value for a solution polymer suggests that branches or entanglements exist in the material. Increasing the Mooney of the Nd-PI resulted in an increase in the $T_{80}$ value and the lack of a measurable cold flow. Presumably this is caused by an increase in physical entanglements as the molecular weight of the polymer increases. A combination of many of these factors, including the lack of a gel fraction, high cis microstructure, narrow molecular weight distribution, and low branching should differentiate the Nd-PI from Ti-PI and Li-PI when physical properties are compared.

Non-Polymer Components.—The consistency of a polymer can be defined by how much of the bulk material consists of non-polymeric components. These components typically include volatiles, extractables, oligomers, and non-combustible residues. Often, these unwanted species can influence the polymer's ultimate properties and limit the applications where it can be used. For example, the presence of isoprene oligomers will cause a material to have an undesirable odor. Likewise, high levels of extractables can be detrimental in applications where long contact times with solvents or solutions are encountered. In an attempt to assess the levels that non-polymeric components exist in Nd-PI, the Nd-PI was compared to Ti-PI and Li-PI, via thermal gravemetric analysis (TGA), Soxhlet extraction, and low molecular weight GPC determination (Table 7).

TABLE 7

Levels of Non-Polymeric Components Found in Different Synthetic Polyisoprenes

| Polymer Type | TGA Volatiles (%) | Methanol/Toluene Extractables (%) | Low Mw (%) | Ash (%) |
|---|---|---|---|---|
| Ti-PI | 1.4 | 0.6 | 3.9 | 0.16 |
| Li-PI | 0.1 | 0.2 | 3.4 | 0.001 |
| Nd-PI | 0.1 | 0.1 | 0.2 | 0.28 |

TGA analysis was used to measure the amount of residual volatile components remaining in the finished polymer. These volatiles typically consist of residual monomer, solvent, moisture, and any low boiling chemicals used in catalyst make-up or as terminating agents. The volatile fraction remaining in Ti-PI was found to be very high, 1.4 weight percent, compared to that measured for Li-PI and Nd-PI. Both of these materials had just 0.1 weight percent volatiles. Soxhlet extraction of each type of polyisoprene, utilizing a 70/30 weight percent solution of methanol/toluene, was used as a measure of residual soluble components present in the finished polymers. Many of these components consist of isoprene dimers, antioxidants, and extremely low molecular weight isoprene oligomers. Again, Ti-PI had the highest levels of solvent extractable residues with 0.6%, followed by Li-PI at 0.2% and Nd-PI with only 0.1%. In an effort to quantify the total percent of low molecular weight residues present in these materials, low molecular weight GPC was performed. In this test, a column set was chosen that discriminated between material with a Mw of less than 2000 g/mol and that with greater than 2000 g/mol. For Ti-PI, the low molecular weight fraction makes up 3.9% of the total polymer, Li-PI had 3.4% of less than 2000 molecular weight components and Nd-PI had just 0.2%. This is a good indication that very low levels of oligomers exist in Nd-PI compared to elevated levels in Ti-PI and Li-PI. The final test the three polyisoprenes were subjected to was an ash test. The percent ash represents the amount of non-volatile, non-extractable, and non-combustible inorganic residues remaining in the polymer. These residues are usually comprised of metal catalyst- and aluminum-oxides left in the finished polymer. As expected, Li-PI had extremely low levels of metal residues where as Ti-PI and Nd-PI had higher levels, 0.16% and 0.28% respectively. The higher level for neodymium could be related to the differences in the molecular weights of neodymium and titanium. Neodymium is three times heavier than titanium on an equal molar basis. Similarly, although neodymium is used at lower levels than titanium, neodymium systems do use large amounts of aluminum alkyl. Nevertheless, from this collection of results, it is quite clear that Nd-PI, with very low levels of volatiles, extractables, and oligomers as compared to Ti-PI and Li-PI, is indeed a very clean source of synthetic polyisoprene.

Compound Properties

Black Filled.—A standard black formulation with 55 phr N299 carbon black and 1.75 phr sulfur was used to compare a low Mooney version of Nd-PI (55 Mooney) with NR, high and low Mooney Ti-PI (80 and 60 Mooney) and Li-PI (48 Mooney) (Table 8). Cured rubber stocks had compounded Mooneys that ranged between 45 for NR up to 56 for high Mooney Ti-PI. All of the synthetic polyisoprene had lower tack than NR, with Ti-PI and Nd-PI being considerably better than Li-PI. This is most likely a result of the higher cis contents found in NR, Ti-PI and Nd-PI. Elongation at break was the shortest for NR (609%) and the longest for Li-PI (749%). Conversely, tensile at break was the highest for NR (25.8 MPa) and the lowest for Li-PI (21.0 MPa). Both Ti-PI and Nd-PI had levels between these two extremes with elongation at break for Ti-PI being 647% and 638% and tensiles of 25.7 MPa and 25.4 MPa. Nd-PI had an elongation of 676% and a tensile of 23.6 MPa. These differences in tensile properties are correlated to the ability of each material to under go strain-induced crystallization. The shorter elongation but higher tensile observed for NR is caused by a stiffening or crystallization as the polymer is stretched. Ti-PI and Nd-PI also display this phenomenon. Li-PI, however, with the longest elongation and lowest tensile is not as efficient at stress induced reinforcement.

TABLE 8

Comparison of Different Types of Polyisoprenes in Black Filled Compounds

| | Polymer | | | | |
|---|---|---|---|---|---|
| | NR | Ti-PI | Ti-PI | Nd-PI | Li-PI |
| Raw Mooney (ML/100° C.) | 90 | 80 | 60 | 55 | 48 |
| Rheometer-ODR (150° C.) | | | | | |
| Max Torque (MH) | 34.5 | 35.6 | 37.5 | 33.9 | 33.5 |
| Min Torque (ML) | 6.5 | 8.4 | 9 | 7 | 8.9 |
| TC 50 | 9.2 | 8.9 | 8.7 | 11.9 | 16.2 |
| TC 90 | 12.8 | 12.2 | 12.0 | 15.4 | 16.2 |
| TS 1 | 4.9 | 5.8 | 5.9 | 6.2 | 6.7 |
| Compound Mooney (ML/100° C.) | 45 | 56.5 | 54.5 | 47 | 54 |
| Tackiness | 34.08 | 19.52 | 19.68 | 15.04 | 9.6 |
| Tensile & Elongation | | | | | |
| Elongation at Break (%) | 609 | 647 | 638 | 676 | 749 |
| 500% Modulus (MPa) | 20.1 | 17.3 | 18.1 | 15.0 | 11.9 |

TABLE 8-continued

Comparison of Different Types of Polyisoprenes in Black Filled Compounds

| | Polymer | | | | |
|---|---|---|---|---|---|
| | NR | Ti-PI | Ti-PI | Nd-PI | Li-PI |
| Shore A Hardness | 61 | 61 | 61 | 57 | 58 |
| Tensile at Break (MPa) | 25.8 | 25.4 | 25.7 | 23.6 | 21.0 |
| Tear Strength (kN/m) | 123.4 | 100.6 | 68.2 | 77.0 | 43.2 |
| Tear Strength Hot (kN/m) | 10.6 | 8.0 | 7.8 | 8.1 | 5.5 |
| Compression Set (%) | 20 | 16.10 | 16.19 | 18.69 | 16.82 |
| Din A Vol. Loss (mm3) | 138.7 | 132 | 136 | 154 | 142.4 |
| Goodyear-Healey Rebound | | | | | |
| Cold Rebound (%) | 11.55 | 11.35 | 11.4 | 11.3 | 11.3 |
| Hot Rebound (%) | 12.7 | 12.65 | 12.7 | 12.6 | 12.6 |

Tear strength results also highlight the differences between NR, Ti-PI, Nd-PI and Li-PI. For example, room temperature tear for NR was 123.4 kN/m, high Mooney Ti-PI had a tear of 100.6 kN/m while the low Mooney Ti-PI tore at 68.2 kN/m. Nd-PI was between the high and low Mooney Ti-PI with a tear strength of 77.0 kN/m. All of these materials were significantly higher than Li-PI, which had a tear strength of just 43.2 kN/m. The same trend was observed for hot tear measured at 100° C. NR had a hot tear of 10.6 kN/m while Ti-PI, high and low Mooney, and Nd-PI had hot tears of 8.0, 7.8, and 8.1 kN/m respectively. Again, these were all significantly higher than Li-PI, which had a hot tear of 5.5 kN/m. Other tests were more closely matched, for example, shore A hardness was measured at 61 for NR and Ti-PI, 57 for Nd-PI, and 58 for Li-PI. Likewise, no differences in hot or cold rebound were detected and only slight variations in compression set measured at 70° C. for 22 hours. It is clear from the collection of these results that Nd-PI displays properties much more closely related to high cis Ti-PI than to Li-PI and could be expected to be a viable replacement for Ti-PI in certain applications.

Gum Stocks.—Comparison of gum stocks was also made (Table 9). The use of lightly filled or fillerless materials is a common practice in the medical and healthcare industries where many of the rubber articles are subjected to only mild stresses. Gum recipes tend to effectively highlight more pronounced differences inherent to a specific type of polymer and not simply the ability of a filler to reinforce a polymer. It is also common to use low levels of curatives in an attempt to keep products as chemically clean as possible. For this reason, a low sulfur formulation using just 0.5 phr sulfur and no filler was chosen for this study.

TABLE 9

Comparison of Different Types of Polyisoprenes in Unfilled Gum Compounds

| | Polymer | | | | | | |
|---|---|---|---|---|---|---|---|
| | NR | Ti-PI | Ti-PI | Nd-PI | Nd-PI | Nd-PI | Li-PI |
| Raw Mooney (ML/100° C.) | 90 | 80 | 60 | 43 | 65 | 80 | 48 |
| Rheometer-ODR (150° C.) | | | | | | | |
| Max Torque (MH) | 26.8 | 28.3 | 27.3 | 26.2 | 25.8 | 25.7 | 25 |
| Min Torque (ML) | 5.8 | 6.6 | 5.7 | 4.6 | 4.8 | 5.2 | 3.4 |
| TC 50 | 4.95 | 6.45 | 6.35 | 6.8 | 6.97 | 6.6 | 8.15 |
| TC 90 | 6.55 | 9.05 | 9 | 9.15 | 9.25 | 9 | 10.45 |
| TS 1 | 3.2 | 3.45 | 3.45 | 3.8 | 3.9 | 3.55 | 4.7 |

TABLE 9-continued

Comparison of Different Types of
Polyisoprenes in Unfilled Gum Compounds

| | Polymer | | | | | | |
|---|---|---|---|---|---|---|---|
| | NR | Ti-PI | Ti-PI | Nd-PI | Nd-PI | Nd-PI | Li-PI |
| Tensile & Elongation | | | | | | | |
| Elongation at Break (%) | 545 | 507 | 508 | 538 | 598 | 586 | 210 |
| 300% Modulus (MPa) | 2.3 | 2.3 | 2.2 | 2.0 | 1.8 | 2.0 | — |
| Shore A Hardness | 46 | 46 | 46 | 46 | 45 | 46 | 45 |
| Tensile at Break (MPa) | 13.2 | 9.7 | 8.4 | 8.7 | 11.9 | 14.9 | 1.3 |
| Tear Strength Orig. (kN/M) | 26.8 | 28.4 | 25.9 | 26.1 | 27.0 | 27.0 | 1.4 |
| Goodyear-Healey Reb. | | | | | | | |
| Cold Rebound (%) | 85.34 | 87.81 | 87.81 | 84.72 | 87.8 | 85.34 | 87.19 |
| Hot Rebound (%) | 81.1 | 90.31 | 90.94 | 90.94 | 90.94 | 92.21 | 90.31 |

A comparison between NR, low and high Mooney Ti-PI, Li-PI and Nd-PI at three different Mooneys (43, 65, and 80) was made. Percent elongation at break was similar for all types of PI except Li-PI. NR, Ti-PI, and Nd-PI all had elongations in the 500% range where as Li-PI dropped to just 210%. 300% modulus was highest for NR at 2.3 MPa and high Mooney Ti-PI at 2.3 Mpa followed by low Mooney Ti-PI at 2.2 MPa. All three Nd-PIs had 300% modulus near 1.9 MPa while Li-PI had failed by 300%. Tensile at break was high for NR measuring 13.2 MPa. High Mooney Ti-PI gave a tensile at break of 9.7 MPa which dropped to 8.4 MPa for the lower Mooney version. Nd-PI followed the trend of higher tensile with higher Mooney. Nd-PI having a Mooney viscosity of 43 had a tensile of 8.7 MPa, 65 Mooney measured 11.9 MPa, and 80 Mooney Nd-PI having a Mooney viscosity of 80 had a tensile at break of 14.9 MPa. This increase in tensile is most likely a result of increased entanglement of polymer chains as the molecular weight increases. Li-PI had very low tensile properties in this formulation measuring only 1.3 MPa at break. Tear strength measurements of these gum stocks also highlighted the differences between the polymers. NR, Ti-PI and Nd-PI all had tear strengths between 25.9 and 28.4 kN/M where as Li-PI had a tear strength of just 1.4 kN/M. Clearly macrostructural differences and strain induced crystallization plays a larger role in these properties in the absence of a reinforcing filler (keeping in mind that black filled Li-PI had tensile strengths only slightly lower than black filled NR, Ti-PI and Nd-PI). Nevertheless, Nd-PI displays gum properties that are similar to NR and Ti-PI while being superior to Li-PI.

A preformed neodymium catalyst system has been identified that is viable for the continuous production of high cis-polyisoprene. Through the proper choice of catalyst levels, and aluminum alkyl ratios, the preparation of a wide range of Mooney viscosities are possible. This Nd-PI has been shown to be gel and oligomer free with low levels of residual volatiles and extractables. Compound results for both black filled and gum stocks indicate this material yields properties that are very similar to high cis titanium polyisoprene. These findings differentiate Nd-PI as an outstanding alternative to Ti-PI and Li-PI in applications where high performance clean synthetic polyisoprene is desired.

Impurities

Example 1

This example serves to show that the levels of impurities in neodymium polyisoprene are lower than those found in titanium polyisoprene. These impurities typically include volatiles, extractables, oligomers, and non-combustible residues. Thermal gravemetric analysis (TGA) was used to quantify the amount of volatile material, as well as ash, present in the polymers. Soxhlet extraction, utilizing a 70/30 weight percent solution of methanol/toluene, was used to measure residual soluble components present in the finished polymers. Low molecular weight GPC was used to determine the amount of oligomers present in the polymer. As is clear from the test results, and in according to the invention, neodymium polyisoprene has significantly less extractables, volatiles and oligomers compared to titanium high cis polyisoprenes.

| Polymer | Extractables | Volatiles | Oligomers | Ash |
|---|---|---|---|---|
| Ti-PI (Natsyn 2200) | 0.6% | 1.4% | 3.9% | 0.2% |
| Ti-PI (Natsyn 2210) | 0.7% | 1.5% | 6.5% | 0.2% |
| Li-PI (Kraton 309) | 0.2% | 0.1% | 3.4% | ND |
| Nd-PI (Purforma) | 0.2% | 0.5% | ND | 0.3% |
| Nd-PI (Purforma) | 0.1% | 0.1% | ND | 0.3% |

ND = not detected

Impurities

Example 2

This example serves to compare a wider class of titanium polyisoprenes with neodymium and lithium polyisoprene. As is clear from the test results, and in accordance with the invention, neodymium polyisoprene has significantly less extractables, volatiles and oligomers compared to the group of titanium high cis polyisoprenes.

| Polymer | Extractables | Volatiles | Oligomers | Ash |
|---|---|---|---|---|
| Natural Rubber | 2.3% | 0.3% | NA | 0.4% |
| Ti-PI (Natsyn) | 1.0% | 0.2%% | 3.7% | 0.2% |
| Ti-PI (SKI-3) | 1.0% | 0.2% | 6.0% | 0.2% |
| Ti-PI (JSR) | 0.9% | 0.2% | 10.3% | 0.1% |
| Ti-PI (Nippon) | 0.5% | 0.3% | ND | 0.2% |
| Nd-PI (Purforma) | 0.4% | 0.2% | ND | 0.2% |
| Nd-PI (Purforma) | 0.4% | 0.3% | ND | 0.2% |
| Li-PI (GDYR) | 0.5% | 0.2% | ND | <0.1% |
| Li-PI (Kraton 307) | 0.2% | 0.2% | ND | ND |
| Li-PI (Kraton 310) | 0.2% | 0.2% | ND | ND |

ND = not detected

The cleanliness of rubber articles prepared with the different polyisoprene rubbers was compared in low sulfur and peroxide cured samples by European Pharmacopoeia (EP) testing in order to determine the amount of oxidizable components in the extracts of the rubber stocks. In the low sulfur cure package the rubber samples were mixed with 2 phr of zinc oxide and 2 phr of stearic acid to make a non-productive compound. Producting compounds were subsequently made by mixing the non-productive compound with 2 phr of methyl tuads accelerator and 0.5 phr of sulfur. In the peroxide cure packages the rubber samples were mixed with 0.4 phr of Di-Cup R peroxide curing agent and 2 phr of Sartomer SR350 co-curing agent.

Cured test sheets having a surface area of approximately 100 cm² were immersed in 100 ml of water that had been purified by reverse osmosis and boiled for 5 minutes. The water was decanted and the samples were rinsed five times with 100 ml the water at room temperature. The washed samples were placed in 250 ml beakers, 200 ml of the water was added, and the beakers were weighed and covered with aluminum foil. Following autoclaving for 30 min at 121° C., the beakers were cooled and re-weighed, with distilled water being added to each beaker to equal the original recorded weight. Then 20 ml of the autoclaved sample extracts were added to a 125 ml beaker with 1 ml 9.8% w/v sulfuric acid and 20 ml of fresh 0.01 N potassium permanganate and boiled for 3 minutes. One gram of potassium iodide was added to each sample after cooling and the mixture was titrated with fresh 0.01 N sodium thiosulfate using an automated potentiometric titrator. Oxidizable components were defined as the titration volume of the blank minus the titration volume for the sample.

| | Oxidizable Components | |
|---|---|---|
| Sample | Sulfur Compound | Peroxide Compound |
| 1 (Natural Rubber) | 9.0 | 4.2 |
| 2 (Ti-PI, Natsyn) | 12.2 | — |
| 3 (Ti-PI, SKI-3) | 8.0 | 4.7 |
| 4 (Ti-PI, JSR) | 11.7 | 5.8 |
| 5 (Ti-PI, Nippon) | 8.0 | 5.3 |
| 6 (Nd-PI, Purforma) | 7.5 | 3.8 |
| 7 (Li-PI, GDY) | 9.4 | 2.8 |
| 8 (Li-PI, Kraton 307) | 8.4 | 3.4 |

As can be seen from the table above, the cured rubber samples made with the neodymium polyisoprene rubber contained less oxidizable components than the samples made with natural rubber or any of the titanium polyisoprene rubbers.

Impurities

Example 3

This example serves to compare the levels of extractables, volatiles, oligomers and ash content in a series of neodymium polyisoprenes that vary in Mooney viscosity. As is clear from the test results neodymium polyisoprene in general has inherently low extractables, volatiles and oligomers and ash.

| Polymer | Extractables | Volatiles | Oligomers | Ash |
|---|---|---|---|---|
| Nd-PI (80 ML) | 0.3% | 0.3% | ND | 0.1% |
| Nd-PI (71 ML) | 0.3% | 0.2% | ND | 0.1% |
| Nd-PI (67 ML) | 0.3% | 0.3% | ND | 0.2% |
| Nd-PI (62 ML) | 0.3% | 0.4% | ND | 0.2% |

ND = not detected

Physical Properties

Examples 1-12

In this series of experiments 12 different rubber samples (natural rubber, neodymium polyisoprene rubber, titanium polyisoprene rubber, and low cis lithium polyisoprene rubber) were compounded and cured. The physical properties of the cured rubber samples were then evaluated and compared.

In the procedure used each of the rubber samples were initially mixed with 2 phr (parts by weight per 100 parts by weight of rubber) of zinc oxide, 1.5 phr of stearic acid, 0.5 phr of wax, and 0.5 phr of Wingstay® S antioxidant to make a non-productive compound. A productive compound was subsequently prepared by mixing the non-productive compound with 1 phr of methyl tuads, 0.5 phr of sulfur, 1.25 phr of Santocure NS TBBS, and 1 phr of Sulfasan R. The compounds were then cured and the physical properties of the samples were evaluated. The tensile strength, elongation at break and tear strength of the cured rubber samples is reported in the following table.

| Rubber | Tensile Strength | Elongation | Tear Strength[12] |
|---|---|---|---|
| Natural | 1912 psi | 545% | 153 ppi |
| Natsyn ® 2200[1] | 1406 psi | 507% | 162 ppi |
| Natsyn ® 2210[2] | 1225 psi | 508% | 148 ppi |
| RNS 7597[3] | 1317 psi | 515% | 154 ppi |
| Neodymium PI[4] | 1255 psi | 538% | 149 ppi |
| Neodymium PI[5] | 1500 psi | 553% | 156 ppi |
| Neodymium PI[6] | 1729 psi | 598% | 154 ppi |
| Neodymium PI[7] | 1422 psi | 559% | 140 ppi |
| Neodymium PI[8] | 2155 psi | 586% | 154 ppi |
| LI PI[9] | 136 psi | 109% | 23 ppi |
| Kraton 309[10] | 194 psi | 210% | 28 ppi |
| Ti PI[11] | 1322 psi | 521% | 150 ppi |

[1]Natsyn ® 2200 is polyisoprene rubber made utilizing a titanium catalyst system.
[2]Natsyn ® 2210 is polyisoprene rubber made utilizing a titanium catalyst system.
[3]RNS 7597 is polyisoprene rubber made utilizing a titanium catalyst system.
[4]Neodymium PI having a Mooney ML 1 + 4 viscosity of 43.
[5]Neodymium PI having a Mooney ML 1 + 4 viscosity of 56.
[6]Neodymium PI having a Mooney ML 1 + 4 viscosity of 65.
[7]Neodymium PI having a Mooney ML 1 + 4 viscosity of 72.
[8]Neodymium PI having a Mooney ML 1 + 4 viscosity of 80.
[9]Polyisoprene synthesized utilizing a lithium catalyst system.
[10]Polyisoprene synthesized utilizing a lithium catalyst system.
[11]Polyisoprene synthesized utilizing a titanium catalyst system.
[12]Original ppi (Die C)

As can be seen from the table above, the compounded samples made with the lithium polyisoprene rubber did not exhibit good physical properties. The cured rubber samples made with titanium polyisoprene rubber had satisfactory physical properties but had high levels of extractable chemical residues. The cured sample made with natural rubber also had satisfactory physical properties but, of course, contained natural rubber protein. Only the cured rubber samples made with neodymium polyisoprene rubber exhibited both good physical properties and low levels of extractable chemical residues.

Physical Properties

Examples 13-17

In this series of experiments 5 different rubber samples (natural rubber, neodymium polyisoprene rubber, titanium polyisoprene rubber, and low cis lithium polyisoprene rubber) were compounded into formulations that were loaded with carbon black and cured. The physical properties of the cured rubber samples were then evaluated and compared.

In the procedure used each of the rubber samples were initially mixed with 4 phr of zinc oxide, 2 phr of stearic acid, 2 phr of Sunolite 240 wax, 1.5 phr of Wingstay® 29 antioxidant, 1.5 phr of Polystay® 100 antioxidant, 55 phr of N299 carbon black, and 10 phr of Sundex 8125 aromatic oil to make a non-productive compound. A productive compound was subsequently prepared by mixing the non-productive compound with 1.75 phr of sulfur and 1 phr of AMAX OBTS accelerator. The compounds were then cured and the physical properties of the samples were evaluated. The tensile strength, elongation at break and tear strength of the cured rubber samples is reported in the following table.

| Rubber | Tensile Strength | Elongation | Tear Strength[5] |
|---|---|---|---|
| Natural | 3738 psi | 609% | 705 ppi |
| Natsyn ® 2200[1] | 3680 psi | 647% | 575 ppi |
| Natsyn ® 2210[2] | 3732 psi | 638% | 390 ppi |
| Neodymium PI[3] | 3420 psi | 676% | 440 ppi |
| Kraton 309[4] | 3048 psi | 749% | 247 ppi |

[1]Natsyn ® 2200 is polyisoprene rubber made utilizing a titanium catalyst system.
[2]Natsyn ® 2210 is polyisoprene rubber made utilizing a titanium catalyst system.
[3]Neodymium PI having a Mooney ML 1 + 4 viscosity of 55.
[4]Polyisoprene synthesized utilizing a lithium catalyst system.
[5]Original ppi (Die B)

As can be seen from the table above, the cured carbon black loaded samples made with the lithium polyisoprene rubber did not exhibit good physical properties. The cured rubber samples made with titanium polyisoprene rubber had satisfactory physical properties but had high levels of extractable chemical residues. The cured sample made with natural rubber also had satisfactory physical properties but, of course, contained natural rubber protein. Only the cured rubber samples made with neodymium polyisoprene rubber exhibited both good physical properties and low levels of extractable chemical residues.

Physical Properties

Examples 18-19

In this experiment a neodymium polyisoprene rubber and a lithium polyisoprene rubber (Kraton 310 lithium polyisoprene rubber) were compounded and cured with a peroxide cure package. The physical properties of the cured rubber samples were then evaluated and compared.

In the procedure used each of the rubber samples were initially mixed with 0.02 phr of Ultramine blue and 10 phr of fumed silica to make a non-productive compound. A productive compound was subsequently prepared by mixing the non-productive compound with 1.66 phr of EF(DBDB)-60 peroxide and 2 phr of Sartomer SR350 peroxide co-curing agent. The compounds were then cured and the physical properties of the samples were evaluated. The tensile strength, elongation at break and tear strength of the cured rubber samples is reported in the following table.

| | Neodymium PI | Lithium PI |
|---|---|---|
| Die C Tear Strength | 23.5 kN/m | 17.9 kN/m |
| Tensile Strength | 1249 psi | 453 psi |
| Elongation | 414% | 262% |

As can be seen from the table above, the neodymium polyisoprene rubber exhibited physical properties that were greatly superior to those of the lithium polyisoprene rubber.

Physical Properties

Examples 20-21

In this experiment the procedure used in Examples 18-19 was repeated expect that the level of silica loading was increased to 20 phr. The physical properties of the cured rubber samples made are reported in the following table.

| | Neodymium PI | Lithium PI |
|---|---|---|
| Die C Tear Strength | 24.9 kN/m | 21.7 kN/m |
| Tensile Strength | 2254 psi | 892 psi |
| Elongation | 505% | 339% |

As can be seen from the table above, the neodymium polyisoprene rubber again exhibited physical properties that were greatly superior to those of the lithium polyisoprene rubber at the higher level of silica loading.

While certain representative embodiments and details have been shown for the purpose of illustrating the subject invention, it will be apparent to those skilled in this art that various changes and modifications can be made therein without departing from the scope of the subject invention.

What is claimed is:

1. A pacifier comprised of a mouth portion having a projecting head and a base portion wherein the mouth portion is comprised of polyisoprene rubber, wherein the polyisoprene rubber is made by a process which comprises polymerizing and terminating the polymerization with an alkaline aqueous neutralizer solution, wherein the neodymium catalyst system is prepared by (1) reacting a neodymium carboxylate with an organoaluminum compound in the presence of isoprene for a period of about 10 minutes to about 30 minutes to produce neodymium-aluminum catalyst component, and (2) subsequently reacting the neodymium-aluminum catalyst component with a dialkyl aluminum chloride for a period of at least 30 minutes to produce the neodymium catalyst systemisoprene monomer in the presence of a neodymium catalyst system.

2. A pacifier as specified in claim 1 wherein the mouth portion is hollow.

3. A pacifier as specified in claim 1 wherein the mouth portion includes at least one recess which is positioned between the projecting head and the base portion.

4. A pacifier as specified in claim 1 wherein the neodymium catalyst is prepared at a temperature that is within the range of about 0° C. to about 100° C.

5. A pacifier as specified in claim 1 wherein the mole ratio of the organoaluminum compound to the neodymium carboxylate is within the range of about 4/1 to about 200/1.

6. A pacifier as specified in claim 5 wherein the organoaluminum compound is selected from the group consisting of trialkylaluminum compounds and dialkylaluminum hydride compounds.

7. A pacifier as specified in claim 6 wherein the molar ratio of the dialkyl aluminum chloride to neodymium is within the range of about 0.5:1 to about 3.5:1.

8. A pacifier as specified in claim 1 wherein the mole ratio of the organoaluminum compound to the neodymium carboxylate is within the range of about 10/1 to about 50/1.

9. A pacifier as specified in claim 1 wherein the polymerization is conducted in an organic solvent.

10. A pacifier as specified in claim 9 wherein the polymerization is carried out at a temperature within the range of about 10 ° C. to about 90 ° C.

11. A pacifier as specified in claim 1 wherein said organoaluminum compound is selected from the group consisting of diethylaluminum hydride, di-n-propylaluminum hydride, di-n-butylaluminum hydride, diisobutylaluminum hydride, diphenylaluminum hydride, di-p-tolylaluminum hydride, dibenzylaluminum hydride, phenylethylaluminum hydride, phenyl-n-propylaluminum hydride, p-tolyethylalumin hydride, p-tolyl-n-propylaluminum hydride, p-tolylisopropylaluminum hydride, benzylethylaluminum hydride, benzyl-n-propylaluminum hydride, benzylisopropylaluminum hydride, ethylaluminium dihydride, butylaluminum dihydride, isobutylaluminum dihydride, octylaluminum dihydride, amylaluminum dihydride, trimethylaluminum, triethylaluminum, tri-n-propylaluminum, triisopropylaluminum, tri-n-propylaluminum, triisopropylaluminum, tri-n-butylaluminum, triisobutytaltuminum, tripentylalumninum, trihexylaluminum, trioctylaluminum, triphenylaluminum, tri-p-tolyaluminum, tribenylaluminum, ethyldiphenylaluminum, ethyl-di-p-tolylaluminum, ethyldibenzylaluminum, diethylphenylaluminum, diethyl-p-tolylaluminum, and diethylbenzylaluminum.

12. A pacifier as specified in claim 7 wherein the dialkyl aluminum chloride is selected from the group consisting of dimethyl aluminum chloride, diethylaluminum chloride, dipropylaluminum chloride, dihexylaluminum chloride, diisobutylaluminum chloride, and didodecyaluminum chloride.

13. A pacifier as specified in claim 1 wherein the molar ratio of isoprene monomer to neodymium ranges from about 5/1 to about 500/1.

14. A pacifier as specified in claim 8 wherein the neodymium carboxylate is selected from the group consisting of neodymium octoate, neodymium neodecanoate, and neodymium 2-ethyl hexanoate.

15. A pacifier as specified in claim 1 wherein after the catalyst is aged in step(2) but prior to the polymerization of isoprene, additional organoaluminum compound is added to the aged catalyst.

16. A pacifier as specified in claim 1 wherein the alkaline aqueous neutralizer solution is an aqueous solution of sodium bicarbonate.

17. A pacifier which is comprised of a mouth portion having a projecting head and a base portion wherein the mouth portion is comprised of polyisoprene rubber, wherein the polyisoprene rubber is made by a process which comprises polymerizing isoprene monomer in the presence of a neodymium catalyst system and terminating the polymerization with an alkaline aqueous neutralizer solution, wherein the neodymium catalyst system is prepared by (1) reacting a neodymium carboxylate with an organoaluminum compound in the presence of isoprene for a period of about 1 minutes to about 12 hours to produce neodymium-aluminum catalyst component, and (2) subsequently reacting the neodymium-aluminum catalyst component with a dialkyl aluminum chloride for a period of at least 30 minutes to produce the neodymium catalyst system, wherein the dialkyl aluminum chloride is added to the neodymium-aluminum catalyst component over a period of at least 30 minutes.

18. A pacifier as specified in claim 17 wherein the neodymium carboxylate is reacted with the organoaluminum compound in the presence of isoprene for a period of 2 hours to about 8 hours at a temperature which is within the range of 0 ° C. to 30 ° C. to produce the neodymium-aluminum catalyst component, wherein the dialkyl aluminum chloride is added to the neodymium-aluminum catalyst component over a period of at least 45 minutes.

19. A pacifier as specified in claim 18 wherein the alkaline aqueous neutralizer solution is an aqueous solution of sodium bicarbonate, and wherein the alkaline aqueous neutralizer solution has a pH within the range of 7.5 to 9.0.

20. A pacifier as specified in claim 16 wherein the alkaline aqueous neutralizer solution has a pH within the range of 8.0 to 8.5.

* * * * *